(12) United States Patent
Fakhoury et al.

(10) Patent No.: US 7,772,243 B2
(45) Date of Patent: Aug. 10, 2010

(54) 4-PHENYLAMINO-QUINAZOLIN-6-YL-AMIDES

(75) Inventors: Stephen Alan Fakhoury, Saline, MI (US); Helen Tsenwhei Lee, Ann Arbor, MI (US); Jessica Elizabeth Reed, Ann Arbor, MI (US); Kevin Matthew Schlosser, Ann Arbor, MI (US); Karen Elaine Sexton, Chelsea, MI (US); Haile Tecle, Ann Arbor, MI (US); Roy Thomas Winters, Pinckney, MI (US)

(73) Assignee: Warner-Lambert Company LLC, Morris Plains, NJ (US)

( * ) Notice: Subject to any disclaimer, the term of this patent is extended or adjusted under 35 U.S.C. 154(b) by 1209 days.

(21) Appl. No.: 11/122,345

(22) Filed: May 5, 2005

(65) Prior Publication Data

US 2005/0250761 A1 Nov. 10, 2005

Related U.S. Application Data

(60) Provisional application No. 60/568,872, filed on May 6, 2004.

(51) Int. Cl.
*A61K 31/517* (2006.01)
*C07D 239/94* (2006.01)
*C07D 413/12* (2006.01)

(52) U.S. Cl. .............. 514/266.21; 514/266.2; 544/119; 544/284; 544/293; 540/600

(58) Field of Classification Search .......... 514/266.2, 514/266.21; 544/284, 293, 119; 540/600
See application file for complete search history.

(56) References Cited

U.S. PATENT DOCUMENTS

| | | | |
|---|---|---|---|
| 5,362,878 A | 11/1994 | Chang et al. |
| 5,366,987 A | 11/1994 | Lee et al. |
| 5,441,975 A | 8/1995 | Lee et al. |
| 5,457,105 A | 10/1995 | Barker |
| 5,486,512 A | 1/1996 | Gregor |
| 5,646,170 A | 7/1997 | Lee et al. |
| 5,656,634 A | 8/1997 | Chang et al. |
| 5,693,657 A | 12/1997 | Lee et al. |
| 5,707,998 A | 1/1998 | Takase et al. |
| 5,736,534 A | 4/1998 | Arnold |
| 5,747,498 A | 5/1998 | Schnur et al. |
| 5,760,041 A | 6/1998 | Wissner et al. |
| 5,770,599 A | 6/1998 | Gibson |
| 5,821,246 A | 10/1998 | Brown et al. |
| 5,929,080 A | 7/1999 | Frost |
| 5,932,574 A | 8/1999 | Baker |
| 5,942,514 A | 8/1999 | Barker |
| 5,955,464 A | 9/1999 | Barker |
| 6,002,008 A | 12/1999 | Wissner et al. |
| 6,008,230 A | 12/1999 | Oku et al. |
| 6,015,814 A | 1/2000 | Barker |
| 6,127,374 A | 10/2000 | Bridges |
| 6,153,617 A | 11/2000 | Bridges |
| 6,184,225 B1 | 2/2001 | Thomas et al. |
| 6,225,318 B1 | 5/2001 | Sobolov-Jaynes et al. |
| 6,251,912 B1 | 6/2001 | Wissner et al. |
| 6,291,455 B1 | 9/2001 | Thomas et al. |
| 6,297,258 B1 | 10/2001 | Wissner et al. |
| 6,323,209 B1 | 11/2001 | Frost |
| 6,344,455 B1 | 2/2002 | Bridges et al. |
| 6,344,459 B1 | 2/2002 | Bridges et al. |
| 6,384,051 B1 | 5/2002 | Frost et al. |
| 6,384,223 B1 | 5/2002 | Gletsos |

(Continued)

FOREIGN PATENT DOCUMENTS

CA 2 403 152 10/2000

(Continued)

OTHER PUBLICATIONS

Discafani, C., et al., "Irreversible Inhibition of Epidermal Growth Factor Receptor Tyrosine Kinase with In Vivo Activity by N-[4-[(3-Bromophenyl)amino]-6-quinazolinyl]-2-butynamide (CL-387,785)," *Biochemical Pharmacology*, 1999, 917-925, vol. 57.

(Continued)

*Primary Examiner*—James O Wilson
*Assistant Examiner*—Tamthom N Truong
(74) *Attorney, Agent, or Firm*—Jeffrey H. Tidwell; Stephen D. Prodnuk; Suzanne M. Bates

(57) ABSTRACT

This invention provides quinazoline compounds of the formula:

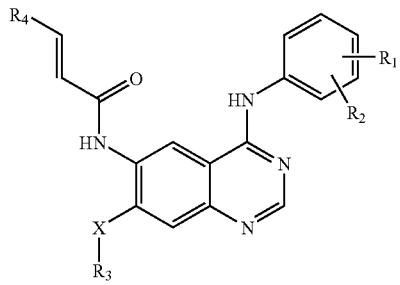

wherein: $R_1$ is halo; $R_2$ is H or halo; $R_3$ is a) $C_1$-$C_3$ alkyl, optionally substituted by halo; or b) —$(CH_2)_n$-morpholino, —$(CH_2)_n$-piperidine, —$(CH_2)_n$-piperazine, —$(CH_2)_n$-piperazine-N($C_1$-$C_3$ alkyl), —$(CH_2)_n$-pyrrolidine, or —$(CH_2)_n$-imidazole; n is 1 to 4; $R_4$ is —$(CH_2)_m$-Het; Het is morpholine, piperidine, piperazine, piperazine-N($C_1$-$C_3$ alkyl), imidazole, pyrrolidine, azepane, 3,4-dihydro-2H-pyridine, or 3,6-dihydro-2H-pyridine, each optionally substituted by alkyl, halo, OH, $NH_2$, NH($C_1$-$C_3$ alkyl) or N ($C_1$-$C_3$ alkyl)$_2$; m is 1-3; and X is O, S or NH; or a pharmaceutically acceptable salt thereof, as well as processes and intermediate compounds for making them, useful pharmaceutical compositions and methods of using the compounds in the treatment of proliferative diseases.

9 Claims, No Drawings

U.S. PATENT DOCUMENTS

| | | | |
|---|---|---|---|
| 6,403,580 B1 | 6/2002 | Himmelsbach et al. | |
| 6,414,148 B1 | 7/2002 | Thomas et al. | |
| 6,476,040 B1 | 11/2002 | Norris et al. | |
| 6,562,818 B1 | 5/2003 | Bridges | |
| 6,617,329 B2 * | 9/2003 | Himmelsbach et al. | 514/252.14 |
| 6,627,634 B2 | 9/2003 | Himmelsbach et al. | |
| 6,653,305 B2 * | 11/2003 | Himmelsbach et al. | .. 514/233.5 |
| 6,664,390 B2 | 12/2003 | Barth et al. | |
| 6,740,651 B2 * | 5/2004 | Himmelsbach et al. | .. 514/228.8 |
| 7,019,012 B2 * | 3/2006 | Himmelsbach et al. | 514/266.22 |
| 7,026,479 B2 | 4/2006 | Boulton et al. | |
| 2002/0049197 A1 | 4/2002 | Himmelsbach et al. | |
| 2002/0077330 A1 | 6/2002 | Himmelsbach et al. | |
| 2002/0082270 A1 | 6/2002 | Himmelsbach et al. | |
| 2002/0082271 A1 | 6/2002 | Himmelsbach et al. | |
| 2002/0115675 A1 | 8/2002 | Himmelsbach et al. | |
| 2002/0173509 A1 | 11/2002 | Himmelsbach et al. | |
| 2002/0193377 A1 | 12/2002 | Andrianjara et al. | |
| 2003/0087881 A1 | 5/2003 | Bridges | |
| 2003/0144506 A1 | 7/2003 | Brown | |
| 2003/0149062 A1 | 8/2003 | Jung et al. | |
| 2003/0158196 A1 | 8/2003 | Jung et al. | |
| 2003/0171386 A1 | 9/2003 | Connell et al. | |
| 2003/0225079 A1 | 12/2003 | Singer et al. | |
| 2004/0034022 A1 | 2/2004 | Barth et al. | |
| 2004/0044014 A1 | 3/2004 | Himmelsbach et al. | |
| 2004/0048887 A1 | 3/2004 | Meade et al. | |
| 2004/0053908 A1 | 3/2004 | Funahashi et al. | |
| 2004/0067942 A1 | 4/2004 | Elliott et al. | |
| 2004/0158065 A1 | 8/2004 | Barth et al. | |
| 2005/0026940 A1 | 2/2005 | Ripin et al. | |
| 2005/0107358 A1 | 5/2005 | Himmelsbach et al. | |
| 2005/0119288 A1 | 6/2005 | Bhattacharya et al. | |
| 2007/0270589 A1 | 11/2007 | Iwamura et al. | |

FOREIGN PATENT DOCUMENTS

| | | |
|---|---|---|
| CA | 2 375 259 | 12/2000 |
| EP | 0 363 212 A2 | 4/1990 |
| EP | 0 566 226 A1 | 10/1993 |
| EP | 0 602 851 A1 | 6/1994 |
| EP | 0 787 722 A1 | 8/1997 |
| EP | 1 369 418 A1 | 12/2003 |
| WO | WO 91/04027 A1 | 4/1991 |
| WO | WO 93/04052 A1 | 3/1993 |
| WO | WO 94/19330 A1 | 9/1994 |
| WO | WO 95/03283 A1 | 2/1995 |
| WO | WO 96/09294 A1 | 3/1996 |
| WO | WO 96/33980 | 10/1996 |
| WO | WO 97/03069 | 1/1997 |
| WO | WO 97/22596 A1 | 6/1997 |
| WO | WO 97/30034 A1 | 8/1997 |
| WO | WO 97/30044 A1 | 8/1997 |
| WO | WO 97/38983 | 10/1997 |
| WO | WO 97/38994 A1 | 10/1997 |
| WO | WO 98/02434 | 1/1998 |
| WO | WO 98/02438 | 1/1998 |
| WO | WO 98/13354 | 4/1998 |
| WO | WO 98/38984 A2 | 9/1998 |
| WO | WO 98/43960 A1 | 10/1998 |
| WO | WO 98/50038 A1 | 11/1998 |
| WO | WO 98/50370 A1 | 11/1998 |
| WO | WO 99/09016 | 2/1999 |
| WO | WO 99/24037 A1 | 5/1999 |
| WO | WO 99/35132 A1 | 7/1999 |
| WO | WO 99/35146 A1 | 7/1999 |
| WO | WO 99/61428 A1 | 12/1999 |
| WO | WO 00/06555 | 2/2000 |
| WO | WO 00/18740 A1 | 4/2000 |
| WO | WO 00/31048 | 6/2000 |
| WO | WO 00/51991 | 9/2000 |
| WO | WO 00/55141 A1 | 9/2000 |
| WO | WO 01/12227 A1 | 2/2001 |
| WO | WO 01/21594 A1 | 3/2001 |
| WO | WO 01/77085 A1 | 10/2001 |
| WO | WO 01/94341 | 12/2001 |
| WO | WO 02/092577 A1 | 11/2002 |
| WO | WO 02/092578 A1 | 11/2002 |
| WO | WO 03/040108 A1 | 5/2003 |
| WO | WO 03/040109 A2 | 5/2003 |
| WO | WO 03/045395 A1 | 6/2003 |
| WO | WO 03/055491 | 7/2003 |
| WO | WO 03/072139 | 9/2003 |
| WO | WO 03/082831 | 10/2003 |
| WO | WO 2004/029045 | 4/2004 |
| WO | WO 2004/064718 A2 | 8/2004 |
| WO | WO 2004/069791 | 8/2004 |
| WO | WO 2004/094410 | 11/2004 |
| WO | WO 2005/040125 A1 | 5/2005 |

OTHER PUBLICATIONS

Rewcastle, G., et al., "Synthesis of 4-(Phenylamino)pyrimidine Derivatives as ATP-Competitive Protein Kinase Inhibitors with Potential for Cancer Chemotherapy," *Current Organic Chemistry*, 2000, 679-706, vol. 4, No. 7.

Singh, P., et al., "Inhibitors of the Epidermal Growth Factor Receptor Protein Tyrosine Kinase: A Quantitative Structure—Activity Relationship Analysis," Journal of Enzyme Inhibition, 1998, 125-134, vol. 13.

Smaill, J., et al., "Tyrosine Kinase Inhibitors. 15. 4-(Phenylamino)quinazoline and 4-(Phenylamino)pyrido[d]pyrimidine Acrylamides as Irreversible Inhibitors of the ATP Binding Site of the Epidermal Growth Factor Receptor," *Journal of Medicinal Chemistry*, 1999, 1803-1815, vol. 42, No. 10.

Smaill, J., et al., "Tyrosine Kinase Inhibitors. 17. Irreversible Inhibitors of the Epidermal Growth Factor Receptor: 4-(Phenylamino)quinazoline- and 4-(Phenylamino)pyrido[3,2-d]pyrimidine-6-acrylamides Bearing Additional Solubilizing Functions," *Journal of Medicinal Chemistry*, 2000, 1380-1397, vol. 43, No. 7.

* cited by examiner

4-PHENYLAMINO-QUINAZOLIN-6-YL-AMIDES

CROSS-REFERENCE TO RELATED APPLICATION(S)

Reference is made to U.S. application Ser. No. 60/568,872, filed May 6, 2004, the disclosure of which is incorporated herein by reference in its entirety.

FIELD OF THE INVENTION

This invention relates to novel compounds which act as inhibitors of tyrosine kinases and are useful in methods of treating, preventing or inhibiting proliferative diseases, including cancer, atherosclerosis, restenosis, endometriosis and psoriasis. Particularly, this invention relates to novel 4-anilino-6-substituted alkenoylamino-quinazoline compounds useful in the treatment of such disorders.

BACKGROUND OF THE INVENTION

Substituted 4-phenylamino-quinazolin-6-yl-amides useful in the treatment of cancer have been described in the art, including those of U.S. Pat. No. 5,457,105 (Barker), U.S. Pat. No. 5,760,041 (Wissner et al.), U.S. Pat. No. 5,770,599 (Gibson), U.S. Pat. No. 5,929,080 (Frost), U.S. Pat. No. 5,955,464 (Barker), U.S. Pat. No. 6,251,912 (Wissner et al.), U.S. Pat. No. 6,344,455 (Bridges et al.), U.S. Pat. No. 6,344,459 (Bridges et al.), U.S. Pat. No. 6,414,148 (Thomas et al.), U.S. Pat. No. 5,770,599 (Gibson et al.), U.S. patent application 2002/0173509 (Himmelsbach et al.), and U.S. Pat. No. 6,323,209 (Frost).

There remains a need for novel and efficacious compounds for the treatment of proliferative disorders.

SUMMARY OF THE INVENTION

This invention comprises quinazoline compounds of Formula I:

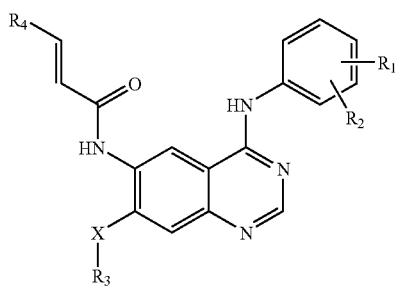

wherein:
$R_1$ is selected from F, Br, Cl or I;
$R_2$ is selected from H, F, Br, Cl or I;
$R_3$ is selected from:
a) $C_1$-$C_3$ straight or branched alkyl, optionally substituted by halogen; or
b) —$(CH_2)_n$-morpholino, —$(CH_2)_n$-piperidine, —$(CH_2)_n$-piperazine, —$(CH_2)_n$-piperazine-N($C_1$-$C_3$ alkyl), —$(CH_2)_n$-pyrrolidine, or —$(CH_2)_n$-imidazole;
n is an integer from 1 to 4;
$R_4$ is —$(CH_2)_m$-Het;
Het is a heterocyclic moiety selected from the group of morpholine, piperidine, piperazine, piperazine-N($C_1$-$C_3$ alkyl), imidazole, pyrrolidine, azepane, 3,4-dihydro-2H-pyridine, or 3,6-dihydro-2H-pyridine, wherein each heterocyclic moiety is optionally substituted by from 1 to 3 groups selected from $C_1$-$C_3$ alkyl, halogen, OH, $NH_2$, NH($C_1$-$C_3$ alkyl) or N ($C_1$-$C_3$ alkyl)$_2$;
m is an integer from 1 to 3; and
X is O, S or NH;
or a pharmaceutically acceptable salt thereof.

This invention also comprises methods of using the compounds of this invention to treat, inhibit, prevent or control the advancement of proliferative diseases including cancer, restenosis, psoriasis, atherosclerosis, or endometriosis, with each of the methods comprising administering a pharmaceutically or therapeutically effective amount of a compound herein to a mammal in need thereof. This invention further comprises pharmaceutical compositions comprising a pharmaceutically effective amount of a compound of this invention and one or more pharmaceutically acceptable excipients and/or carriers. This invention also comprises synthetic routes and intermediate compounds useful in the preparation of the compounds herein.

DETAILED DESCRIPTION OF THE INVENTION

One group of compounds of this invention comprises those described above wherein $R_1$ is a halogen and $R_2$ is hydrogen. Another comprises compounds wherein $R_1$ is fluorine and $R_2$ is another halogen. A further group comprises those in which $R_1$ is 4-fluoro and $R_2$ is 3-chloro.

Another group of compounds of this invention comprises those of Formula II:

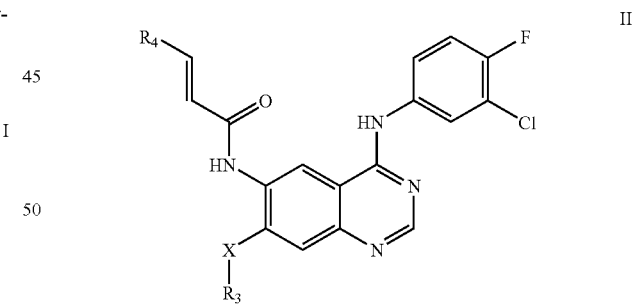

wherein:
$R_3$ is selected from:
a) $C_1$-$C_3$ straight or branched alkyl, optionally substituted by halogen; or
b) —$(CH_2)_q$-morpholino, —$(CH_2)_q$-piperidine, —$(CH_2)_q$-piperazine, —$(CH_2)_q$-piperazine-N($C_1$-$C_3$ alkyl), —$(CH_2)_q$-pyrrolidine, or —$(CH_2)_q$-imidazole;
q is an integer from 1 to 2;
$R_4$ is —$(CH_2)_m$-Het;
Het is a piperidine, piperazine, piperazine-N($C_1$-$C_3$ alkyl), imidazole, pyrrolidine, azepane or dihydropyridine group, optionally substituted by 1 or 2 groups selected from halogen or $C_1$-$C_3$ alkyl;

m is an integer from 1 to 3; and

X is O, S or NH;

or a pharmaceutically acceptable salt thereof.

A further group of compounds of this invention comprises those of Formula III:

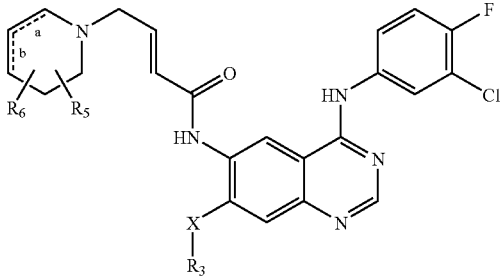

III wherein:

$R_3$ is $C_1$-$C_3$ straight or branched alkyl, optionally substituted by halogen;

$R_5$ and $R_6$ are independently selected from H, $C_1$-$C_3$ alkyl, F, Br, I or Cl;

X is O, S or NH; and the dashed lines designated a and b each indicate an optional double bond, with the proviso that only a single double bond a or b exists in one compound;

or a pharmaceutically acceptable salt form thereof.

A subset of each of the groups of compounds described herein comprises those in which X is O. Other subsets include those in which X is NH or S. Another subset of each group herein comprises compounds in which X is O and $R_3$ is $C_1$-$C_3$ straight or branched alkyl optionally substituted by from 1 to 3 halogen atoms. Another subset includes compounds in which $R_3$ is a polyfluorinated $C_2$-$C_3$ alkyl, such as 1,1,2,2-tetrafluoroethyl or 2,2,3,3,3-pentafluoropropyl groups, or perfluorinated $C_2$-$C_3$ alkyl, such as a pentafluoroethyl or heptafluoropropyl group. It will be understood that the $C_1$-$C_3$ straight or branched alkyl groups defined as $R_3$ in the groups herein may be halogenated by one or more halogen groups, including perhalogenation, i.e. having the maximum number of halogens allowed by the valence limitations of the alkyl group (i.e. $R_3$ is trifluoromethyl, pentafluoroethyl, heptafluoropropyl, etc.).

The compounds of this invention may be used to inhibit the activity of tyrosine kinases, particularly including erbB1, erbB2 and erbB4. The compounds of this invention may be used in methods to treat, inhibit, prevent or control the advancement of proliferative diseases including cancer, restenosis, psoriasis, atherosclerosis, or endometriosis. Cell proliferative disorders that may be treated by these methods include cancers, skeletal disorders, angiogenic or blood vessel proliferative disorders, fibrotic disorders and mesangial cell proliferative disorders. Fibrotic proliferative disorders, i.e. the abnormal formation of extracellular matrices, that may be treated with these compounds and methods include atherosclerosis, hepatic cirrhosis and mesangial cell proliferative disorders (including human renal diseases, such as glomerulonephritis, diabetic nephropathy, malignant nephrosclerosis, thrombotic microangiopathy syndromes, transplant rejection, and glomerulopathies). Each of the methods described herein comprise administering to a mammal in need thereof a pharmaceutically or therapeutically effective amount of a compound of this invention, or a pharmaceutically acceptable salt form thereof.

This invention also provides a method for treating or inhibiting polycystic kidney disease in a mammal, the method comprising administering to a mammal experiencing polycystic kidney disease a pharmaceutically effective amount of a compound of this invention. This method applies to polycystic kidney disease of both the autosomal recesive and autosomal dominant forms.

In addition, this invention also provides a method for treating or inhibiting colonic polyps in a mammal, the method comprising administering to a mammal experiencing polycystic kidney disease a pharmaceutically effective amount of a compound of this invention. Methods of inhibition of colonic polyps are understood to include methods which reduce the rate of growth of colonic polyps. The methods for treating or inhibiting colonic polyps in mammals may also include co-administration or cyclic regimens utilizing additional pharmaceutically effective agents, such as COX-2 inhibitors including celecoxib; rofecoxib; valdecoxib; lumiracoxib (also known as COX-189); LAS-34475; UR-8880; 2-(3,4-Difluorophenyl)-4-(3-hydroxy-3-methyl-butoxy)-5-[4-methylsulfonyl)phenyl]-3(2H)-pyridazinone (ABT-963); 3-[(3-chlorophenyl)[4-(methylsulfonyl)phenyl]methylene]dihydro-2(3H)-Furanone (BMS-347070); Tilacoxib; The compound 4-[5-(2,4-difluorophenyl)-4,5-dihydro-3-(trifluoromethyl)-1H-pyrazol-1-yl]-benzenesulfonamide (also known as E 6087); CS-502 [Chemical Abstracts Service Registry Number ("CAS Reg. No.") 176429-82-6]; (6aR,10aR)-3-(1,1-dimethylheptyl)-6a,7,10,10a-tetrahydro-1-hydroxy-6,6-dimethyl-6H-dibenzo[b,d]pyran-9-carboxylic acid ("CT-3"); CV-247; 2(5H)-Furanone, 5,5-dimethyl-3-(1-methylethoxy)-4-[4-(methylsulfonyl)phenyl]-("DFP"); carprofen; deracoxib; Etoricoxib (tradename ARCOXIA® by MERCK & CO., Inc., Whitehouse Station, N.J.); GW-406381; aspirin; Tiracoxib; Meloxicam; Nimesulide; 2-(Acetyloxy)benzoic acid, 3-[(nitrooxy)methyl]phenyl ester ("NCX-4016"); Parecoxib (trade name application pending for DYNASTAT® by G. D. Searle & Co., Skokie, Ill.); N-Acetyl-L-threonyl-L-prolyl-L-arginyl-D-prolyl-L-glutaminyl-L-seryl-L-histidyl-L-asparaginyl-L-α-aspartylglycyl-L-α-aspartyl-L-phenylalanyl-L-α-glutamyl-L-α-glutamyl-L-isoleucyl-L-prolyl-L-α-glutamyl-L-α-glutamyl-L-tyrosyl-L-leucyl-L-glutamine (also known as P54, CAS Reg. No. 130996-28-0); Rofecoxib (tradename VIOXX® by MERCK & CO., Inc., Whitehouse Station, N.J.); RevIMiD; 2,6-Bis(1,1-dimethylethyl)-4-[(E)-(2-ethyl-1,1-dioxo-5-isothiazolidinylidene)methyl]phenol ("S-2474"); 5(R)-Thio-6-sulfonamide-3(2H)-benzofuranone ("SVT-2016"); and N-[3-(Formylamino)-4-oxo-6-phenoxy-4H-1-benzopyran-7-yl]-methanesulfonamide ("T-614"); or a pharmaceutically acceptable salt thereof.

This invention also relates to a method for the treatment of abnormal cell growth in a mammal, including a human, comprising administering to said mammal an amount of a compound of the formula 1, as defined above, or a pharmaceutically acceptable salt, solvate or prodrug thereof, that is effective in treating abnormal cell growth. In one embodiment of this method, the abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In one embodiment the method comprises comprising administering to a mammal an amount of a compound of formula 1 that is effective in treating said cancer solid tumor. In one preferred embodiment the solid tumor is breast, lung, colon, brain, prostate, stomach, pancreatic, ovarian, skin (melanoma), endocrine, uterine, testicular, and bladder cancer.

In another embodiment of said method, said abnormal cell growth is a benign proliferative disease, including, but not limited to, psoriasis, benign prostatic hypertrophy or restinosis.

This invention also relates to a method for the treatment of abnormal cell growth in a mammal which comprises administering to said mammal an amount of a compound of formula 1, or a pharmaceutically acceptable salt, solvate or prodrug thereof, that is effective in treating abnormal cell growth in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

This invention also relates to a pharmaceutical composition for the treatment of abnormal cell growth in a mammal, including a human, comprising an amount of a compound of the formula 1, as defined above, or a pharmaceutically acceptable salt, solvate or prodrug thereof, that is effective in treating abnormal cell growth, and a pharmaceutically acceptable carrier. In one embodiment of said composition, said abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said pharmaceutical composition, said abnormal cell growth is a benign proliferative disease, including, but not limited to, psoriasis, benign prostatic hypertrophy or restinosis.

This invention also relates to a method for the treatment of abnormal cell growth in a mammal which comprises administering to said mammal an amount of a compound of formula 1, or a pharmaceutically acceptable salt, solvate or prodrug thereof, that is effective in treating abnormal cell growth in combination with another anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens. The invention also contemplates a pharmaceutical composition for treating abnormal cell growth wherein the composition includes a compound of formula 1, as defined above, or a pharmaceutically acceptable salt, solvate or prodrug thereof, that is effective in treating abnormal cell growth, and another anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

This invention also relates to a method for the treatment of a disorder associated with angiogenesis in a mammal, including a human, comprising administering to said mammal an amount of a compound of the formula 1, as defined above, or a pharmaceutically acceptable salt, solvate or prodrug thereof, that is effective in treating said disorder in combination with one or more anti-tumor agents listed above. Such disorders include cancerous tumors such as melanoma; ocular disorders such as age-related macular degeneration, presumed ocular histoplasmosis syndrome, and retinal neovascularization from proliferative diabetic retinopathy; rheumatoid arthritis; bone loss disorders such as osteoporosis, Paget's disease, humoral hypercalcemia of malignancy, hypercalcemia from tumors metastatic to bone, and osteoporosis induced by glucocorticoid treatment; coronary restenosis; and certain microbial infections including those associated with microbial pathogens selected from adenovirus, hantaviruses, *Borrelia burgdorferi, Yersinia* spp., *Bordetella pertussis*, and group A *Streptococcus*.

This invention also relates to a method of (and to a pharmaceutical composition for) treating abnormal cell growth in a mammal which comprise an amount of a compound of formula 1, or a pharmaceutically acceptable salt, solvate or prodrug thereof, in combination with an amount of one or more substances selected from anti-angiogenesis agents, signal transduction inhibitors, and antiproliferative agents, which amounts are together effective in treating said abnormal cell growth.

Anti-angiogenesis agents, such as MMP-2 (matrix-metalloprotienase 2) inhibitors, MMP-9 (matrix-metalloproteinase 9) inhibitors, and COX-II (cyclooxygenase II) inhibitors, can be used in conjunction with a compound of formula 1 in the methods and pharmaceutical compositions described herein. Examples of useful COX-II inhibitors include CELEBREX™ (celecoxib), Bextra (valdecoxib), paracoxib, Vioxx (rofecoxib), and Arcoxia (etoricoxib). Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 331, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No.

99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are herein incorporated by reference in their entirety. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in combination with the compounds of the present invention are AG-3340, RO 32-3555, RS 13-0830, and the compounds recited in the following list: 3-[[4-(4-fluoro-phenoxy)-benzenesulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo[3.2.1]octane-3-carboxylic acid hydroxyamide; (2R, 3R) 1-[4-(2-chloro-4-fluoro-benzyloxy)-benzenesulfonyl]-3-hydroxy-3-methyl-piperidine-2-carboxylic acid hydroxyamide; 4-[4-(4-fluoro-phenoxy)-benzenesulfonylamino]-tetrahydro-pyran-4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide; 3-[4-(4-chloro-phenoxy)-benzenesulfonylamino]-tetrahydro-pyran-3-carboxylic acid hydroxyamide; (2R, 3R) 1-[4-(4-fluoro-2-methyl-benzyloxy)-benzenesulfonyl]-3-hydroxy-3-methyl-piperidine-2-carboxylic acid hydroxyamide; 3-[[4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid; 3-exo-3-[4-(4-chloro-phenoxy)-benzenesulfonylamino]-8-oxa-bicyclo[3.2.1]octane-3-carboxylic acid hydroxyamide;

3-endo-3-[4-(4-fluoro-phenoxy)-benzenesulfonylamino]-8-oxa-bicyclo[3.2.1]octane-3-carboxylic acid hydroxyamide; and 3-[4-(4-fluoro-phenoxy)-benzenesulfonylamino]-tetrahydro-furan-3-carboxylic acid hydroxyamide; and pharmaceutically acceptable salts, solvates and prodrugs of said compounds.

VEGF inhibitors, for example, SU-11248, SU-5416 and SU-6668 (Sugen Inc. of South San Francisco, Calif., USA), can also be combined with a compound of formula 1. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), U.S. Pat. No. 6,653,308 (issued Nov. 25, 2003), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are herein incorporated by reference in their entirety. Other examples of some specific VEGF inhibitors are IM862 (Cytran Inc. of Kirkland, Wash., USA); Avastin, an anti-VEGF monoclonal antibody of Genentech, Inc. of South San Francisco, Calif.; and angiozyme, a synthetic ribozyme from Ribozyme (Boulder, Colo.) and Chiron (Emeryville, Calif.).

ErbB2 receptor inhibitors, such as GW-282974 (Glaxo Wellcome plc), CP-724,714 (Pfizer Inc.), and the monoclonal antibodies AR-209 (Aronex Pharmaceuticals Inc. of The Woodlands, Texas, USA) and 2B-1 (Chiron), may be administered in combination with a compound of formula 1. Such erbB2 inhibitors also include Herceptin, 2C4, and pertuzumab. Such erbB2 inhibitors include those described in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), each of which is herein incorporated by reference in its entirety. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are herein incorporated by reference in their entirety. Other erbb2 receptor inhibitors include TAK-165 (Takeda) and GW-572016 (Glaxo-Wellcome).

Various other compounds, such as styrene derivatives, have also been shown to possess tyrosine kinase inhibitory properties, and some of tyrosine kinase inhibitors have been identified as erbB2 receptor inhibitors. More recently, five European patent publications, namely EP 0 566 226 A1 (published Oct. 20, 1993), EP 0 602 851 A1 (published Jun. 22, 1994), EP 0 635 507 A1 (published Jan. 25, 1995), EP 0 635 498 A1 (published Jan. 25, 1995), and EP 0 520 722 A1 (published Dec. 30, 1992), refer to certain bicyclic derivatives, in particular quinazoline derivatives, as possessing anti-cancer properties that result from their tyrosine kinase inhibitory properties. Also, World Patent Application WO 92/20642 (published Nov. 26, 1992), refers to certain bis-mono and bicyclic aryl and heteroaryl compounds as tyrosine kinase inhibitors that are useful in inhibiting abnormal cell proliferation. World Patent Applications WO96/16960 (published Jun. 6, 1996), WO 96/09294 (published Mar. 6, 1996), WO 97/30034 (published Aug. 21, 1997), WO 98/02434 (published Jan. 22, 1998), WO 98/02437 (published Jan. 22, 1998), and WO 98/02438 (published Jan. 22, 1998), also refer to substituted bicyclic heteroaromatic derivatives as tyrosine kinase inhibitors that are useful for the same purpose. Other patent applications that refer to anti-cancer compounds are World Patent Application WO00/44728 (published Aug. 3, 2000), EP 1029853A1 (published Aug. 23, 2000), and WO01/98277 (published Dec. 12, 2001) all of which are incorporated herein by reference in their entirety.

Other antiproliferative agents that may be used with the compounds of the present invention include inhibitors of the enzyme farnesyl protein transferase and inhibitors of the receptor tyrosine kinase PDGFr, including the compounds disclosed and claimed in the following U.S. patent application Ser. No. 09/221946 (filed Dec. 28, 1998); Ser. No. 09/454058 (filed Dec. 2, 1999); Ser. No. 09/501163 (filed Feb. 9, 2000); Ser. No. 09/539930 (filed Mar. 31, 2000); Ser. No. 09/202796 (filed May 22, 1997); Ser. No. 09/384339 (filed Aug. 26, 1999); and Ser. No. 09/383755 (filed Aug. 26, 1999); and the compounds disclosed and claimed in the following U.S. provisional patent applications 60/168207 (filed Nov. 30, 1999); 60/170119 (filed Dec. 10, 1999); 60/177718 (filed Jan. 21, 2000); 60/168217 (filed Nov. 30, 1999), and 60/200834 (filed May 1, 2000). Each of the foregoing patent applications and provisional patent applications is herein incorporated by reference in their entirety.

A compound of formula 1 may also be used with other agents useful in treating abnormal cell growth or cancer, including, but not limited to, agents capable of enhancing antitumor immune responses, such as CTLA4 (cytotoxic lymphocyte antigen 4) antibodies, and other agents capable of blocking CTLA4; and anti-proliferative agents such as other farnesyl protein transferase inhibitors, for example the farnesyl protein transferase inhibitors described in the references cited in the "Background" section, supra. Specific CTLA4 antibodies that can be used in the present invention include those described in U.S. Provisional Application 60/113,647 (filed Dec. 23, 1998) which is herein incorporated by reference in its entirety.

A compound of formula I may be applied as a sole therapy or may involve one or more other anti-tumor substances, for example those selected from, for example, mitotic inhibitors, for example vinblastine; alkylating agents, for example cisplatin, oxaliplatin, carboplatin and cyclophosphamide; antimetabolites, for example 5-fluorouracil, capecitabine, cytosine arabinoside and hydroxyurea, or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex (tamoxifen) or, for example anti-androgens such as Casodex (4'-cyano-3-(4-fluorophenylsulphonyl)-2-hydroxy-2-methyl-3'-(trifluoromethyl)propionanilide).

The compounds of the present invention may be used alone or in combination with one or more of a variety of anti-cancer agents or supportive care agents. For example, the compounds of the present invention may be used with cytotoxic agents, e.g., one or more selected from the group consisting of a camptothecin, irinotecan HCl (Camptosar), edotecarin, SU-11248, epirubicin (Ellence), docetaxel (Taxotere), paclitaxel, rituximab (Rituxan) bevacizumab (Avastin), imatinib mesylate (Gleevac), Erbitux, gefitinib (Iressa), and combinations thereof. The invention also contemplates the use of the compounds of the present invention together with hormonal therapy, e.g., exemestane (Aromasin), Lupron, anastrozole (Arimidex), tamoxifen citrate (Nolvadex), Trelstar, and combinations thereof. Further, the invention provides a compound of the present invention alone or in combination with one or more supportive care products, e.g., a product selected from the group consisting of Filgrastim (Neupogen), ondansetron (Zofran), Fragmin, Procrit, Aloxi, Emend, or combinations thereof. Such conjoint treatment may be achieved by way of the simultaneous, sequential or separate dosing of the individual components of the treatment.

The compounds of the invention may be used with antitumor agents, alkylating agents, antimetabolites, antibiotics, plant-derived antitumor agents, camptothecin derivatives, tyrosine kinase inhibitors, antibodies, interferons, and/or biological response modifiers. In this regard, the following is a non-limiting list of examples of secondary agents that may be used with the compounds of the invention.

Alkylating agents include, but are not limited to, nitrogen mustard N-oxide, cyclophosphamide, ifosfamide, melphalan, busulfan, mitobronitol, carboquone, thiotepa, ranimustine, nimustine, temozolomide, AMD-473, altretamine, AP-5280, apaziquone, brostallicin, bendamustine, carmustine, estramustine, fotemustine, glufosfamide, ifosfamide, KW-2170, mafosfamide, and mitolactol; platinum-coordinated alkylating compounds include but are not limited to, cisplatin, carboplatin, eptaplatin, lobaplatin, nedaplatin, oxaliplatin or satrplatin;

Antimetabolites include but are not limited to, methotrexate, 6-mercaptopurine riboside, mercaptopurine, 5-fluorouracil (5-FU) alone or in combination with leucovorin, tegafur, UFT, doxifluridine, carmofur, cytarabine, cytarabine ocfosfate, enocitabine, S-1, gemcitabine, fludarabin, 5-azacitidine, capecitabine, cladribine, clofarabine, decitabine, eflornithine, ethynylcytidine, cytosine arabinoside, hydroxyurea, TS-1, melphalan, nelarabine, nolatrexed, ocfosfate, disodium premetrexed, pentostatin, pelitrexol, raltitrexed, triapine, trimetrexate, vidarabine, vincristine, vinorelbine; or for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid;

Antibiotics include but are not limited to: aclarubicin, actinomycin D, amrubicin, annamycin, bleomycin, daunorubicin, doxorubicin, elsamitrucin, epirubicin, galarubicin, idarubicin, mitomycin C, nemorubicin, neocarzinostatin, peplomycin, pirarubicin, rebeccamycin, stimalamer, streptozocin, valrubicin or zinostatin;

Hormonal therapy agents, e.g., exemestane (Aromasin), Lupron, anastrozole (Arimidex), doxercalciferol, fadrozole, formestane, anti-estrogens such as tamoxifen citrate (Nolvadex) and fulvestrant, Trelstar, toremifene, raloxifene, lasofoxifene, letrozole (Femara), or anti-androgens such as bicalutamide, flutamide, mifepristone, nilutamide, Casodex® (4'-cyano-3-(4-fluorophenylsulphonyl)-2-hydroxy-2-methyl-3'-(trifluoromethyl)propionanilide) and combinations thereof;

Plant derived anti-tumor substances include for example those selected from mitotic inhibitors, for example vinblastine, docetaxel (Taxotere) and paclitaxel;

Cytotoxic topoisomerase inhibiting agents include one or more agents selected from the group consisting of aclarubicn, amonafide, belotecan, camptothecin, 10-hydroxycamptothecin, 9-aminocamptothecin, diflomotecan, irinotecan HCl (Camptosar), edotecarin, epirubicin (Ellence), etoposide, exatecan, gimatecan, lurtotecan, mitoxantrone, pirarubicin, pixantrone, rubitecan, sobuzoxane, SN-38, tafluposide, and topotecan, and combinations thereof;

Immunologicals include interferons and numerous other immune enhancing agents. Interferons include interferon alpha, interferon alpha-2a, interferon, alpha-2b, interferon beta, interferon gamma-1a or interferon gamma-n1. Other agents include filgrastim, lentinan, sizofilan, TheraCys, ubenimex, WF-10, aldesleukin, alemtuzumab, BAM-002, dacarbazine, daclizumab, denileukin, gemtuzumab ozogamicin, ibritumomab, imiquimod, lenograstim, lentinan, melanoma vaccine (Corixa), molgramostim, OncoVAX-CL, sargramostim, tasonermin, tecleukin, thymalasin, tositumomab, Virulizin, Z-100, epratuzumab, mitumomab, oregovomab, pemtumomab, Provenge;

Biological response modifiers are agents that modify defense mechanisms of living organisms or biological responses, such as survival, growth, or differentiation of tissue cells to direct them to have anti-tumor activity. Such agents include krestin, lentinan, sizofiran, picibanil, or ubenimex.

Other anticancer agents include alitretinoin, ampligen, atrasentan bexarotene, bortezomib. Bosentan, calcitriol, exisulind, finasteride, fotemustine, ibandronic acid, miltefosine, mitoxantrone, I-asparaginase, procarbazine, dacarbazine, hydroxycarbamide, pegaspargase, pentostatin, tazarotne, TLK-286, Velcade, Tarceva, or tretinoin;

Other anti-angiogenic compounds include acitretin, fenretinide, thalidomide, zoledronic acid, angiostatin, aplidine, cilengtide, combretastatin A-4, endostatin, halofuginone, rebimastat, removab, Revlimid, squalamine, ukrain and Vitaxin;

Platinum-coordinated compounds include but are not limited to, cisplatin, carboplatin, nedaplatin, or oxaliplatin;

Camptothecin derivatives include but are not limited to camptothecin, 10-hydroxycamptothecin, 9-aminocamptothecin, irinotecan, SN-38, edotecarin, and topotecan;

Tyrosine kinase inhibitors are Iressa or SU5416;

Antibodies include Herceptin, Erbitux, Avastin, or Rituximab;

Interferons include interferon alpha, interferon alpha-2a, interferon, alpha-2b, interferon beta, interferon gamma-1a or interferon gamma-n1;

Biological response modifiers are agents that modify defense mechanisms of living organisms or biological responses, such as survival, growth, or differentiation of tissue cells to direct them to have anti-tumor activity. Such agents include krestin, lentinan, sizofiran, picibanil, or ubenimex; and Other antitumor agents include mitoxantrone, I-asparaginase, procarbazine, dacarbazine, hydroxycarbamide, pentostatin, or tretinoin.

"Abnormal cell growth", as used herein, unless otherwise indicated, refers to cell growth that is independent of normal regulatory mechanisms (e.g., loss of contact inhibition). This includes the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (4) any tumors that proliferate by receptor tyrosine kinases; (5) any tumors that proliferate by aberrant serine/threonine kinase activation; and (6) benign and malignant cells of other proliferative diseases in which aberrant serine/threonine kinase activation occurs.

This invention also provides methods for inhibiting tyrosine kinases in a mammal, the method comprising administering to a mammal in need thereof a pharmaceutically or therapeutically effective amount of a compound of this invention, or a pharmaceutically acceptable salt form thereof. More particularly, this invention further provides a method for irreversibly inhibiting tyrosine kinases in a mammal.

The methods herein also include methods for irreversibly inhibiting tyrosine kinases, including EGFR, PDGFR, c-src, erbB1, erbB2 and erbB4. This invention may also be characterized as including a method for inhibiting VEGF secretion in a mammal. A further method comprises the inhibition of tyrosine phosphorylation of erbB3 in a mammal. The compounds herein are also useful as pan-erbB inhibitors, i.e. inhibiting multiple erbB kinases with each administration.

Those skilled in the art can readily identify patients in need of the treatments described herein. For instance, those at higher risk of developing restenosis include individuals who have undergone angioplasty, bypass or graft procedures, or been the recipients of other vascular procedures or trauma. Individuals at greater risk of developing atherosclerosis include those who are obese, consume high fat diets, have elevated cholesterol levels, or have hypertension. The methods herein are useful in the treatment of mammals including humans, companion animals such as dogs and cats, and farm animals, such as horses, sheep, hogs, goats, cattle, etc.

The term "cancer" includes, but is not limited to, the following cancers: breast; ovary; cervix; prostate; testis; esophagus; glioblastoma; neuroblastoma; stomach; skin, keratoacanthoma; lung, epidermoid carcinoma, large cell carcinoma, adenocarcinoma, small cell lung; non-small cell lung; bone; colon, adenocarcinoma, adenoma; pancreas, adenocarcinoma;thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkins, hairy cells;buccal cavity and pharynx (oral), lip, tongue, mouth, pharynx; small intestine; colon-rectum, large intestine, rectum; brain and central nervous system; and leukemia.

In addition, compounds of this invention can be used to treat patients in need of inhibition vascular endothelial growth factor (VEGF) secretion. Patients in need of inhibition of VEGF secretion include those having cancer, diabetic retinopathy, rheumatoid arthritis, psoriasis, restenosis, atherosclerosis, osteoporosis, endometriosis, persons undergoing embryo implantation, or persons having other diseases in which angiogenesis or neovascularization plays a role.

The compounds of the present invention can be used in methods to inhibit the tyrosine phosphorylation of erbB1, erbB2 and erbB4. Patients in need of inhibition of tyrosine phosphorylation of erbB1, erbB2 and erbB4 are patients having or at risk of having the diseases mentioned herein with regard to the inhibition of EGFR and the inhibition of VEGF secretion.

The compounds herein can be administered to humans and animals either orally, rectally, parenterally (intravenously, intramuscularly or subcutaneously), intracisternally, intravaginally, intraperitoneally, intravesically, locally (powders, ointments, or drops), or as a buccal or nasal spray. The compound can be administered alone or as part of a pharmaceutically acceptable composition that includes pharmaceutically acceptable excipients.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents, or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants. The compounds of this invention may be readily adapted to aqueous formulations. For example, 4-Piperidin-1-yl-but-2-enoic acid [4-(3-chloro-4-fluoro-phenylamino)-7-methoxy-quinazolin-6-yl]-amide has an aqueous solubility of about 10 µg/mL at pH 6.3 and solubility increases at lower pHs.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft- and hard-filled gelatin capsules using such excipients as lactose or milk sugar, as well as high molecular weight polyethylene-glycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound in a certain part of the intestinal tract in a delayed manner. Examples of embedding compositions that can be used are polymeric substances and waxes. The active compound can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compound, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

This invention also comprises pharmaceutically or therapeutically acceptable salts, esters, amides and prodrug forms of the compounds of this invention. The terms "pharmaceutically acceptable salts, esters, amides, and prodrugs" as used herein refer to those carboxylate salts, amino acid addition salts, esters, amides, and prodrugs of the compound of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compound or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactobionate and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine and the like (see, for example, S. M. Berge, et al., "Pharmaceutical Salts," J. Pharm. Sci., 1977;66: 1-19 which is incorporated herein by reference).

Examples of pharmaceutically acceptable, non-toxic esters of the compounds of this invention include $C_1$-$C_6$ alkyl esters wherein the alkyl group is a straight or branched chain. Acceptable esters also include $C_5$-$C_7$ cycloalkyl esters as well as arylalkyl esters such as, but not limited to benzyl. $C_1$-$C_4$ alkyl esters are preferred. Esters of the compound of the present invention may be prepared according to conventional methods.

Examples of pharmaceutically acceptable, non-toxic amides of the compound of this invention include amides derived from ammonia, primary $C_1$-$C_6$ alkyl amines and secondary $C_1$-$C_6$ dialkyl amines wherein the alkyl groups are straight or branched chain. In the case of secondary amines, the amine may also be in the form of a 5- or 6-membered heterocycle containing one nitrogen atom. Amides derived from ammonia, $C_1$-$C_3$ alkyl primary amines and $C_1$-$C_2$ dialkyl secondary amines are preferred. Amides of the compound of the invention may be prepared according to conventional methods.

The term "prodrug" refers to compounds that are rapidly transformed in vivo to yield the parent compound of the above formulas, for example, by hydrolysis in blood. A thorough discussion is provided in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are incorporated herein by reference.

The compound of the present invention can be administered to a patient at pharmaceutically or therapeutically effective dosage levels in the range of about 0.1 to about 1,000 mg per day. For a normal human adult having a body weight of about 70 kg, a dosage in the range of about 0.01 to about 100 mg per kilogram of body weight per day is sufficient. The specific dosage used, however, can vary. For example, the dosage can depend on a number of factors including the requirements of the patient, the severity of the condition being treated, and the pharmacological activity of the compound being used. The determination of optimum dosages for a particular patient is well known to those skilled in the art. One dosage regimen in humans comprises administration of a compound of this invention, such as 4-piperidin-1-yl-but-2-enoic acid [4-(3-chloro-4-fluoro-phenylamino)-7-methoxy-quinazolin-6-yl]-amide or a pharmaceutically acceptable salt, ester or amide form thereof, at a dosage range of from about 500 mg to about 1,000 mg per day in a single or divided doses. Pharmaceutically useful compositions for use in this regimen may comprise individual dosage forms containing 100 mg, 200 mg, 250 mg, 500 mg or 1,000 mg of the active compound and one or more pharmaceutically acceptable carriers or excipients.

The invention compounds can be formulated in conventional manners to provide convenient dosage forms for delivery to mammals by various routes, including oral, parenteral (i.e., subcutaneous, intravenous, and intramuscular), transdermal, e.g., slow release skin patch or cream, as well as by slow release delivery devices such as osmotic pumps, suppositories, and buccal seals. The following non-limiting examples further illustrate how the compounds of this invention may be readily formulated.

| 100 mg Tablet Formulation | | | |
|---|---|---|---|
| Per Tablet (g) | | | Per 10,000 Tablets (g) |
| 0.10 | 4-Piperidin-1-yl-but-2-enoic acid [4-(3-chloro-4-fluoro-phenylamino)-7-methoxy-quinazolin-6-yl]-amide | | 1000 |
| 0.080 | Lactose | | 800 |
| 0.010 | Corn starch (for mix) | | 100 |
| 0.008 | Corn starch (for paste) | | 80 |
| 0.148 | | | 1480 |
| 0.002 | Magnesium stearate (1%) | | 20 |
| 0.150 | | | 1500 |

The active agent of this invention, lactose, and corn starch (for mix) are blended to uniformity. The corn starch (for paste) is suspended in 600 mL of water and heated with stirring to form a paste. This paste is used to granulate the mixed powders. The wet granules are passed through a No. 8 hand screen and dried at 80° C. The dry granules are then passed through a No.16 screen. The mixture is lubricated with 1% magnesium stearate and compressed into tablets in a conventional tableting machine. The tablets are useful for treating cancers such as breast, prostate, lung, ovarian, colon, pancreatic, melanoma, esophageal, brain, Kaposi's sarcoma, and lymphomas.

| Preparation of Oral Suspension | |
|---|---|
| Ingredient | Amount |
| 4-Piperidin-1-yl-but-2-enoic acid [4-(3-chloro-4-fluoro-phenylamino)-7-methoxy-quinazolin-6-yl]-amide | 500 mg |
| Sorbitol solution (70% N.F.) | 40 mL |
| Sodium benzoate | 150 mg |

| -continued | |
|---|---|
| Preparation of Oral Suspension | |
| Ingredient | Amount |
| Saccharin | 10 mg |
| Cherry flavor | 50 mg |
| Distilled water qs | 100 mL |

The sorbitol solution is added to 40 mL of distilled water, and the pyrido pyrimidine is suspended therein. The saccharin, sodium benzoate, and flavoring are added and dissolved. The volume is adjusted to 100 mL with distilled water. Each milliliter of syrup contains 5 mg of invention compound.

Preparation of Parenteral Solution

In a solution of 700 mL of propylene glycol and 200 mL of water for injection is suspended 20.0 g of 4-Piperidin-1-yl-but-2-enoic acid [4-(3-chloro-4-fluoro-phenylamino)-7-methoxy-quinazolin-6-yl]-amide with stirring. After suspension is complete, the pH is adjusted to 5.5 with hydrochloric acid, and the volume is made up to 1000 mL with water for injection. The formulation is sterilized, filled into 5.0 mL ampoules, each containing 2.0 mL (representing 40 mg of invention compound) and sealed under nitrogen.

Suppositories

A mixture of 400 mg of 4-Piperidin-1-yl-but-2-enoic acid [4-(3-chloro-4-fluoro-phenylamino)-7-methoxy-quinazolin-6-yl]-amide, and 600 mg of theobroma oil is stirred at 60° C. to uniformity. The mixture is cooled and allowed to harden in a tapered mold to provide a 1 g suppository.

Slow Release Formulation

Five hundred milligrams of 4-Piperidin-1-yl-but-2-enoic acid [4-(3-chloro-4-fluoro-phenylamino)-7-methoxy-quinazolin-6-yl]-amide is converted to a hydrochloride salt and placed into an Oros osmotic pump for controlled release for treatment of atherosclerosis.

Skin Patch Formulation

One hundred milligrams of 4-Piperidin-1-yl-but-2-enoic acid [4-(3-chloro-4-fluoro-phenylamino)-7-methoxy-quinazolin-6-yl]-amide is admixed with 100 mg of propylene glycol monolaurate in a polydimethylsiloxane adhesive. The mixture is layered onto an elastic film made with an adhesive formulation of polybutene, polyisobutylene, and propylene glycol monolaurate. The layers are placed between 2 layers of polyurethane film. A release liner is attached to the adhesive surface, and is removed prior to application to a skin surface. The propylene glycol monolaurate serves as a permeation-enhancing agent.

The compound of the present invention can exist in unsolvated as well as solvated forms with pharmaceutically acceptable solvents such as water, ethanol, and the like. In general, the solvated forms are considered equivalent to the unsolvated forms for the purposes of the present invention. It is intended that the compound in question be either synthetically produced or biologically produced, such as through metabolism.

A pharmaceutically or therapeutically effective amount of a compound herein will be understood to be an amount sufficient to inhibit the activity of the proteins and phosphorylation mechanisms described herein in a mammal to a degree that limits, inhibits or prevents the progress and development of the proliferative disease or other tyrosine kinase-mediated malady in question. A pharmaceutically or therapeutically effective amount, in reference to the treatment, inhibition, prevention or control of the advancement of a cell proliferative disorder may also be understood to be an amount sufficient to bring about cell death, inhibit the growth of cells causing the disorder, relieve discomfort due to the disorder, or the prolong the life of a patient experiencing the disorder.

Non-limiting examples of compounds representing the scope of this invention include:

4-Piperidin-1-yl-but-2-enoic acid [4(3-chloro-4-fluoro-phenylamino)-7-methoxy-quinazolin-6-yl]-amide;
4-Piperidin-1-yl-but-2-enoic acid [4(3-chloro-4-fluoro-phenylamino)-7-methylsulfanyl-quinazolin-6-yl]-amide;
4-Piperidin-1-yl-but-2-enoic acid [4(3-chloro-4-fluoro-phenylamino)-7-methylamino-quinazolin-6-yl]-amide;
4-Piperidin-1-yl-but-2-enoic acid [4(3-chloro-4-fluoro-phenylamino)-7-isopropoxy-quinazolin-6-yl]-amide;
4-Piperidin-1-yl-but-2-enoic acid [4(3-bromo-phenylamino)-7-methoxy-quinazolin-6-yl]-amide;
4-Piperidin-1-yl-but-2-enoic acid [4(3-chloro-4-fluoro-phenylamino)-7-ethoxy-quinazolin-6-yl]-amide;
4-Piperidin-1-yl-but-2-enoic acid [4(3-chloro4-fluoro-phenylamino)-7-propoxy-quinazolin-6-yl]-amide;
4-(4-Fluoro-piperidin-1-yl)-but-2-enoic acid [4-(3-chloro-4-fluoro-phenylamino)-7-methoxy-quinazolin-6-yl]-amide;
4-(3-Fluoro-piperidin-1-yl)-but-2-enoic acid [4-(3-chloro-4-fluoro-phenylamino)-7-methoxy-quinazolin-6-yl]-amide;
4-(2-Fluoro-piperidin-1-yl)-but-2-enoic acid [4-(3-chloro-4-fluoro-phenylamino)-7-methoxy-quinazolin-6-yl]-amide;
4-Morpholin-4-yl-but-2-enoic acid [4(3-chloro-4-fluoro-phenylamino)-7-methoxy-quinazolin-6-yl]-amide;
4-Azepan-1-yl-but-2-enoic acid [4-(3-chloro-4-fluoro-phenylamino)-7-methoxy-quinazolin-6-yl]-amide;
4-Piperidin-1-yl-but-2-enoic acid [4(3-chloro-4-fluoro-phenylamino)-7-trifluoromethoxy-quinazolin-6-yl]-amide;
4-Piperidin-1-yl-but-2-enoic acid [4(3-chloro-4-fluoro-phenylamino)-7-fluoromethoxy-quinazolin-6-yl]-amide;
4-Piperidin-1-yl-but-2-enoic acid [4(3-chloro-4-fluoro-phenylamino)-7-fluoroethoxy-quinazolin-6-yl]-amide;
4-Piperidin-1-yl-but-2-enoic acid [4(3-chloro-4-fluoro-phenylamino)-7-(2-fluoro-ethylsulfanyl)-quinazolin-6-yl]-amide;
4-Piperidin-1-yl-but-2-enoic acid [4(3-chloro-4-fluoro-phenylamino)-7-trifluoroethoxy-quinazolin-6-yl]-amide;
4-Piperidin-1-yl-but-2-enoic acid [4(3-chloro-4-fluoro-phenylamino)-7-difluoroethoxy-quinazolin-6-yl]-amide;
4-Piperidin-1-yl-but-2-enoic acid [4(3-chloro-4-fluoro-phenylamino)-7-(3-morpholin-4-yl-propoxy)-quinazolin-6-yl]-amide;
4-Piperidin-1-yl-but-2-enoic acid [4(3-chloro-4-fluoro-phenylamino)-7-(2-piperidin-1-ethoxy)-quinazolin-6-yl]-amide;
4-(3,4-Dihydro-2H-pyridin-1-yl)-but-2-enoic acid [4(3-chloro-4-fluoro-phenylamino)-7-methoxy-quinazolin-6-yl]amide;
4-(3,4-Dihydro-2H-pyridin-1-yl)-but-2-enoic acid [4(3-chloro-4-fluoro-phenylamino)-7-ethoxy-quinazolin-6-yl]amide;
4-(3,4-Dihydro-2H-pyridin-1-yl)-but-2-enoic acid [4(3-chloro-4-fluoro-phenylamino)-7-methylsulfanyl-quinazolin-6-yl]amide;
4-(3,4-Dihydro-2H-pyridin-1-yl)-but-2-enoic acid [4(3-chloro-4-fluoro-phenylamino)-7-fluoroethoxy-quinazolin-6-yl]amide;
4-(3,6-Dihydro-2H-pyridin-1-yl)-but-2-enoic acid [4(3-chloro-4-fluoro-phenylamino)-7-methoxy-quinazolin-6-yl]amide;
4-(3,6-Dihydro-2H-pyridin-1-yl)-but-2-enoic acid [4(3-chloro4-fluoro-phenylamino)-7-methoxy-quinazolin-6-yl]amide;
4-(3,6-Dihydro-2H-pyridin-1-yl)-but-2-enoic acid [4(3-chloro-4-fluoro-phenylamino)-7-fluoroethoxy-quinazolin-6-yl]amide;
4-(3,6-Dihydro-2H-pyridin-1-yl)-but-2-enoic acid [4(3-chloro-4-fluoro-phenylamino)-7-methylsufanyl-quinazolin-6-yl]amide;
4-Piperazin-1-yl-but-2-enoic acid [4(3-chloro-4-fluoro-phenylamino)-7-methoxy-quinazolin-6-yl]amide;
4-(4-Methyl-piperazin-1-yl)-but-2-enoic acid [4(3-chloro-4-fluoro-phenylamino)-7-methoxy-quinazolin-6-yl]amide;
4-Imidazol-1-yl-but-2-enoic acid [4(3-chloro-4-fluoro-phenylamino)-7-methoxy-quinazolin-6-yl]amide;
4-Pyrrolidin-1-yl-but-2-enoic acid [4(3-chloro-4-fluoro-phenylamino)-7-methoxy-quinazolin-6-yl]amide;
5-Piperidin-1-yl-pent-2-enoic acid [4(3-chloro-4-fluoro-phenylamino)-7-methoxy-quinazolin-6-yl]-amide;
5-Piperidin-1-yl-pent-2-enoic acid [4(3-chloro-4-fluoro-phenylamino)-7-methylsulfanyl-quinazolin-6-yl]-amide;
5-Piperidin-1-yl-pent-2-enoic acid [4(3-chloro-4-fluoro-phenylamino)-7-methylamino-quinazolin-6-yl]-amide;
5-Piperidin-1-yl-pent-2-enoic acid [4(3-chloro-4-fluoro-phenylamino)-7-isopropoxy-quinazolin-6-yl]-amide;
5-Piperidin-1-yl-pent-2-enoic acid [4(3-bromo-phenylamino)-7-methoxy-quinazolin-6-yl]-amide;
5-Piperidin-1-yl-pent-2-enoic acid [4(3-chloro-4-fluoro-phenylamino)-7-ethoxy-quinazolin-6-yl]-amide;
5-Piperidin-1-yl-pent-2-enoic acid [4(3-chloro4-fluoro-phenylamino)-7-propoxy-quinazolin-6-yl]-amide;
5-(4-Fluoro-piperidin-1-yl)-pent-2-enoic acid [4-(3-chloro-4-fluoro-phenylamino)-7-methoxy-quinazolin-6-yl]-amide;
5-(3-Fluoro-piperidin-1-yl)-pent-2-enoic acid [4-(3-chloro-4-fluoro-phenylamino)-7-methoxy-quinazolin-6-yl]-amide;
5-(2-Fluoro-piperidin-1-yl)-pent-2-enoic acid [4-(3-chloro4-fluoro-phenylamino)-7-methoxy-quinazolin-6-yl]-amide;
5-Morpholin-4-yl-pent-2-enoic acid [4(3-chloro-4-fluoro-phenylamino)-7-methoxy-quinazolin-6-yl]-amide;
5-Azepan-1-yl-pent-2-enoic acid [4-(3-chloro-4-fluoro-phenylamino)-7-methoxy-quinazolin-6-yl]-amide;
5-Piperidin-1-yl-pent-2-enoic acid [4(3-chloro-4-fluoro-phenylamino)-7-trifluoromethoxy-quinazolin-6-yl]-amide;
5-Piperidin-1-yl-pent-2-enoic acid [4(3-chloro-4-fluoro-phenylamino)-7-fluoromethoxy-quinazolin-6-yl]-amide;
5-Piperidin-1-yl-pent-2-enoic acid [4(3-chloro-4-fluoro-phenylamino)-7-fluoroethoxy-quinazolin-6-yl]-amide;
5-Piperidin-1-yl-pent-2-enoic acid [4(3-chloro-4-fluoro-phenylamino)-7-(2-fluoro-ethylsulfanyl)-quinazolin-6-yl]-amide;
5-Piperidin-1-yl-pent-2-enoic acid [4(3-chloro-4-fluoro-phenylamino)-7-trifluoroethoxy-quinazolin-6-yl]-amide;

5-Piperidin-1-yl-pent-2-enoic acid [4(3-chloro-4-fluoro-phenylamino)-7-difluoroethoxy-quinazolin-6-yl]-amide;

5-Piperidin-1-yl-pent-2-enoic acid [4(3-chloro-4-fluoro-phenylamino)-7-(3-morpholin-4-yl-propoxy)-quinazolin-6-yl]-amide;

5-Piperidin-1-yl-pent-2-enoic acid [4(3-chloro-4-fluoro-phenylamino)-7-(2-piperidin-1-yl-ethoxy)-quinazolin-6-yl]-amide;

6-Piperidin-1-yl-hex-2-enoic acid [4-(3-chloro-4-fluoro-phenylamino)-7-methoxy-quinazolin-6-yl]-amide;

6-Piperidin-1-yl-hex-2-enoic acid [4-(3-chloro-4-fluoro-phenylamino)-7-methylsulfanyl-quinazolin-6-yl]-amide;

6-Piperidin-1-yl-hex-2-enoic acid [4-(3-chloro-4-fluoro-phenylamino)-7-methylamino-quinazolin-6-yl]-amide;

6-Piperidin-1-yl-hex-2-enoic acid [4-(3-chloro-4-fluoro-phenylamino)-7-ethoxy-quinazolin-6-yl]-amide; and 6-Piperidin-1-yl-hex-2-enoic acid [4-(3-chloro-4-fluoro-phenylamino)-7-fluoroethoxy-quinazolin-6-yl]-amide;

or a pharmaceutically acceptable salt form thereof.

Compounds of this invention may be prepared using methods and materials known in the art. Compounds of this invention wherein X is oxygen may be prepared as illustrated in the following Scheme 1, wherein the 4-position aniline group is represented a 4-fluoro-3-chloro aniline group.

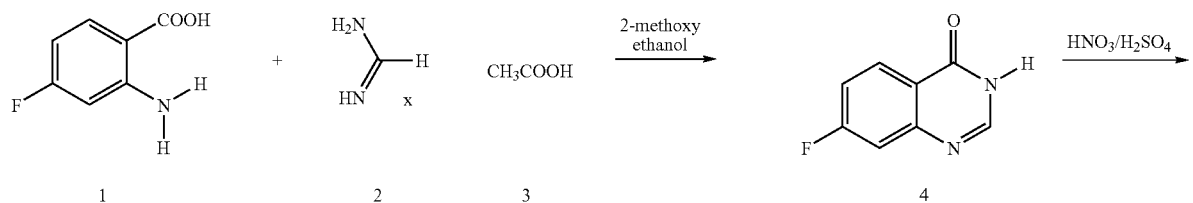

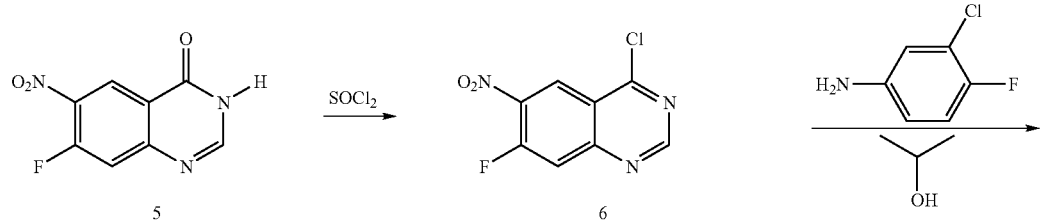

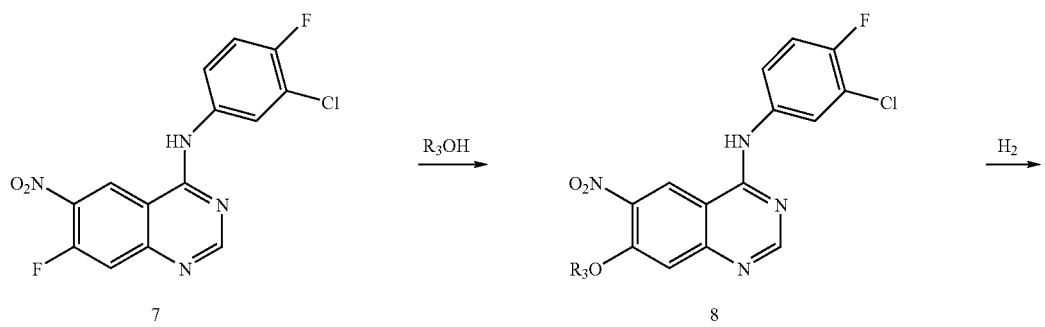

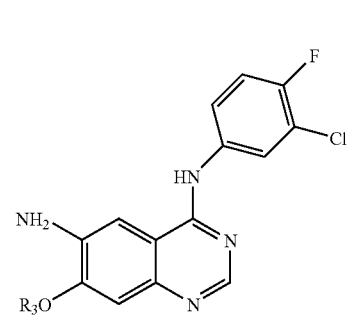

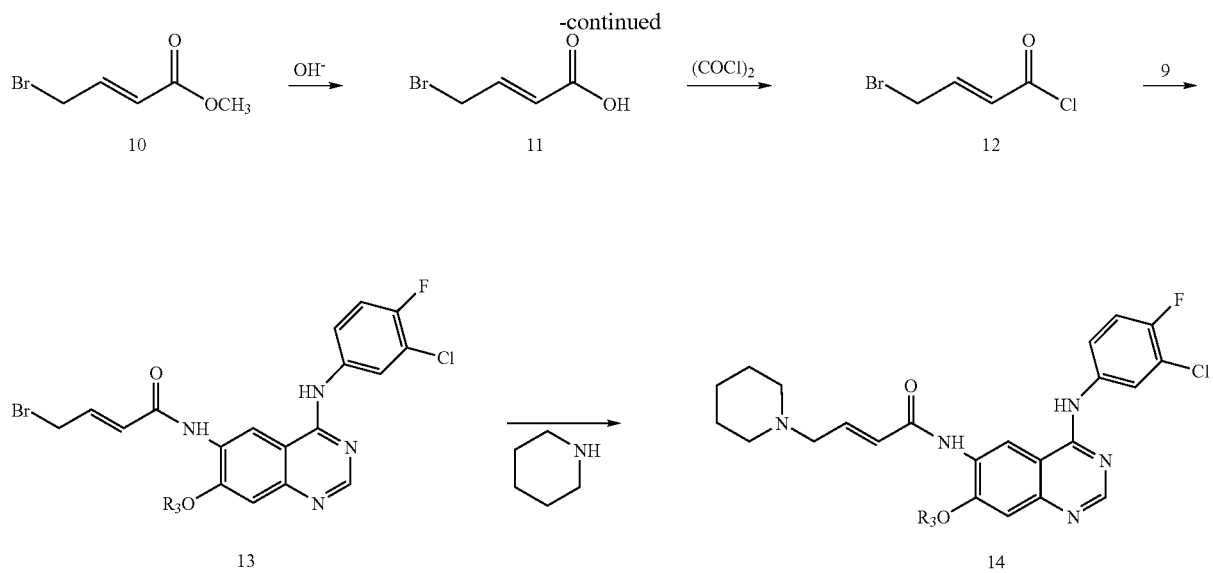

4-Chloro-7-fluoro-6-nitroquinazoline (7) can be prepared by methods similar to those described in J.Med. Chem. 1996, 39, 918-928. Generally, 2-amino-4-fluoro-benzoic acid (1) can be reacted with formamidine (2) and acetic acid (3) in the presence of 2-methoxyethanol to provide 7-Fluoro-3H-quinazolin-4-one (4). The 7-fluoro-3H-quinazolin-4-one (4) can be nitrated to 7-fluoro-6-nitro-3H-quinazolin-4-one (5), which can be treated with thionyl chloride to yield 4-chloro-6-nitro-7-fluoro-3H-quinazoline (6). The 4-chloro-quinazoline compound (6) can be combined with a desirably substituted aniline, represented above by 4-fluoro-3-chloro-aniline, in the presence of a tertiary amine and isopropanol to provide the 4-anilino-6-nitro-7-fluoro-quinazoline (7).

The 4-anilino-6-nitro-7-fluoro-quinazoline (7) may be reacted with an alcohol of the formula $R_3OH$, wherein $R_3$ is as defined above, to yield the 7-alkoxylated compound (8). Reduction of the 6-nitro compound (8) provides the 6-amino analog (9).

The 6-position amino compound (9) may be reacted with a haloalkenoyl chloride (12), such as a 4-bromo-but-2-enoyl chloride, 5-bromo-pent-2-enoyl chloride, 4-chloro-but-2-enoyl chloride, or 5-chloro-pent-2-enoyl chloride, to provide an alkenoic acid[4-anilino]-7-alkoxylated-quinazolin-6-yl-amide (13). Haloalkenoyl chloride agents useful in this scheme may be prepared by methods known in the art, such as the treatment of a relevant haloalkenoic acid, represented by bromoalkenoic acid ester (10), with a primary alcohol, yielding the corresponding haloalkenoic acid (11), which may in turn be treated with oxalyl chloride to provide the desired haloalkenoyl chloride (12).

Finally, the quinazoline-6-alkanoic acid compound (13) may be treated with a cyclic amine, such as piperidine, piperazine, etc., to provide the desired final compound (14).

It will be understood that compounds herein having the 7-position alkoxy groups can be prepared as above using an alcohol of the formula $R_3OH$, wherein $R_3$ is an alkyl group as defined herein, known in the art including, but not limited to, methanol, ethanol, propanol, isopropanol, fluoromethanol, chloromethanol, difluoromethanol, dichloromethanol, trifluoromethanol, trichloromethanol, 1-fluoroethanol, 2-fluroethanol, 2-chloroethanol, 2-iodoethanol, 2-bromoethanol, 1,1-difluoroethanol, 2,2-difluoroethanol, 2,2-dichloroethanol, 1,2,2-trifluorethanol, 2,2,2-trifluorethanol, 1,1,2,2-tetrafluorethanol, pentafluoroethanol, 3-fluoro-1-propanol, 2,3-difluoro-1-propanol, 3,3-difluoro-1-propanol, 2,3,3-trifluoro-1-propanol, 3,3,3-trifluoro-1-propanol, 1,1,3-trifluoro-1-propanol, 1,2,2,3-tetrafluoro-1-propanol, 2,3,3,3-tetrafluoro-propanol, 2,2,3,3,3-pentafluoro-1-propanol, 1,2,3,3,3-pentafluoro-1-propanol, 1,1,2,3,3,3-hexafluoro-1-propanol, heptafluoro-1-propanol, 2-fluoro-2-propanol, 1,1,-difluoro-2-propanol, 1,3-difluoro-2-propanol, 1-fluoro-2-propanol, 1,1,1-trifluoro-2-propanol, 1,1,3,3-tetrafluoro-2-propanol, 1,1,3,3,3-pentafluoro-2-propanol, 1,1,2,3,3-hexafluoro-2-propanol, 1,1,1,3,3,3-hexafluoro-2-propanol, 1,1,1,2,3,3,3,-heptafluoro-2-propanol, etc.

Within the scope of this invention are useful intermediate compounds of the formula:

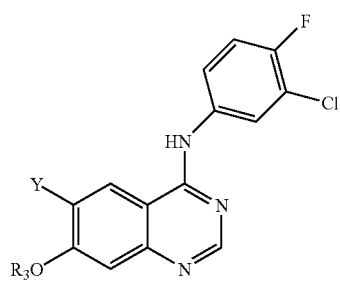

wherein:
Y is $NO_2$, $NH_2$, or the moiety halo-$(CH_2)_m$—CH=CH—C(O)—$NH_2$—;
halo is F, Cl, Br or I;
m is an integer from 1 to 3;
$R_3$ is selected from:
a) a mono-, di- or tri-halogenated methyl group;
b) $C_2$-$C_3$ straight or branched alkyl, optionally substituted by halogen; or
c) —$(CH_2)_m$-morpholino, —$(CH_2)_n$-piperidine, —$(CH_2)_n$- piperazine, —$(CH_2)_n$-piperazine-NC($C_1$-$C_3$ alkyl), —$(CH_2)_n$-pyrrolidine, or —$(CH_2)_n$-imidazole.

23

These compounds specifically include those of the formulae above wherein R₃ is an ethane, propane, isopropane, fluoromethane, chloromethane, difluoromethane, dichloromethane, trifluoromethane, trichloromethane, 1-fluoroethane, 2-fluroethane, 2-chloroethane, 2-iodoethane, 2-bromoethane, 1,1-difluoroethane, 2,2-difluoroethane, 2,2-dichloroethane, 1,2,2-trifluorethane, 2,2,2-trifluorethane, 1,1,2,2-tetrafluorethane, pentafluoroethane, 3-fluoro-1-propane, 2,3-difluoro-1-propane, 3,3-difluoro-1-propane, 2,3,3-trifluoro-1-propane, 3,3,3-trifluoro-1-propane, 1,1,3-trifluoro-1-propane, 1,2,2,3-tetrafluoro-1-propane, 2,3,3,3-tetrafluoro-propane, 2,2,3,3,3-pentafluoro-1-propane, 1,2,3,3,3-pentafluoro-1-propane, 1,1,2,3,3,3-hexafluoro-1-propane, heptafluoro-1-propane, 2-fluoro-2-propane, 1,1,-difluoro-2-propane, 1,3-difluoro-2-propane, 1-fluoro-2-propane, 1,1,1-trifluoro-2-propane, 1,1,3,3-tetrafluoro-2-propane, 1,1,3,3,3-pentafluoro-2-propane, 1,1,2,3,3-hexafluoro-2-propane, 1,1,1,3,3,3-hexafluoro-2-propane, or 1,1,1,2,3,3,3,-heptafluoro-2-propane group.

Compounds of this invention wherein X is sulfur may be prepared as illustrated in the following Scheme 1 by replacing the alcohol R₃OH reacted with the (3-Chloro-4-fluoro-phenyl)-(7-halo-6-nitro-3,4-dihydro-quinolin-4-yl)-amine (Compound 7) with an appropriate alkylthiol of the formula R₃SH, wherein R₃ is as defined herein. Useful alkylthiol compounds of the formula R₃SH include, but are not limited to, methanethiol, ethanethiol, 1-propanethiol, 2-propanethiol, fluoromethanethiol, 2-fluoroethanethiol, 2,2-difluoro-ethanethiol, 2,2,2-trifluoro-ethanethiol, etc.

Similarly, compounds of this invention wherein X is —NH— may be prepared as illustrated in the following Scheme 1 by replacing the alcohol R₃OH reacted with the (3-Chloro-4-fluoro-phenyl)-(7-halo-6-nitro-3,4-dihydro-quinolin-4-yl)-amine (Compound 7) with an appropriate alkylamine of the formula R₃NH, wherein R₃ is as defined herein. Useful alkylamines include, but are not limited to, methylamine, ethylamine, propylamine, isopropylamine, 1-fluoromethylamine, 1,1-difluoromethylamine, 1,1,1-trifluoromethylamine, 2-fluoroethylamine, 2,2-difluoroethylamine, 2,2,2-trifluoroethylamine, 3-fluoropropylamine, 3,3-difluoropropylamine, 3,3,3-trifluoropropylamine, 2,3,3-tetrafluoropropylamine, 2,2,3,3,3-pentafluoropropylamine, 1,1,2,2,3,3,3-heptafluoropropylamine, etc.

Piperidine compounds useful in the preparing R⁴ groups in the compounds of this invention include, but are not limited to piperidine, 2-Fluoro-piperidine, 3-Fluoro-piperidine, 4-Fluoro-piperidine, 4-Bromo-piperidine, 4-Chloro-piperidine, 2-Hydroxy-piperidine, 3-Hydroxy-Propyl-piperidine, 2-Methyl-piperidine, 3-Methyl-piperidine, 4-Methyl-piperidine, 4-Ethyl-piperidine, 4-Propyl-piperidine, 2-Amino-piperidine, 3-Amino-piperidine, 4-Amino-piperidine, 2-Methyl-piperidine, 2,3-Dimethyl-piperidine, 3,3-Dimethyl-piperidine, 2,4-Dimethyl-piperidine, 2,5-Dimethyl-piperidine, 2,6-Dimethyl-piperidine, 3,5-Dimethyl-piperidine, 2-Methyl-5-ethyl-piperidine, 3-Methyl-4-hydroxy-piperine, 2,6-Dimethyl-4-hydroxy-piperidine, 2,5-Dimethyl-4-hydroxy-piperidine, 2,3-Dimethyl-4-hydroxy-piperidine, 3,3-Difluoro-piperidine, 4,4-Difluoro-piperidine, 4,4-Dihydroxy-piperidine, 2,4,6-Trimethyl-piperidine, etc.

24

EXAMPLE 1

4-Piperidin-1-yl-but-2-enoic acid [4-(3-chloro-4-fluoro-phenylamino)-7-(2-fluoro-ethoxy)-quinazolin-6-yl]-amide

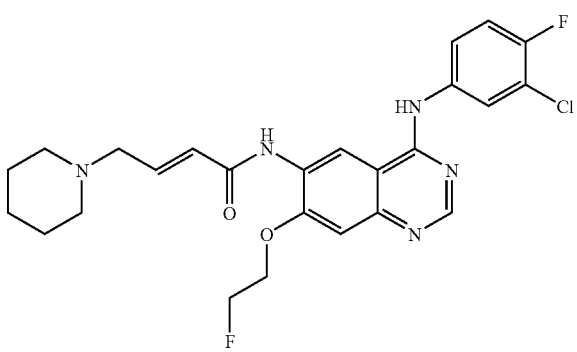

7-fluoro-6-nitro-4-chloroquinazoline (14.73,g, 65 mmol) was combined with 3-choro-4-fluoroaniline (9.49 g, 65 mmol) and triethylamine (10 mL, 72 mmol) in 150 mL of isopropanol. The reaction was stirred at room temperature for 1.5 hours, resulting in a yellow slurry. The solid was collected by filtration, rinsing with isopropanol and then water. The solid was dried in a 40° C. vacuum oven overnight to give 19.83 g (91%) of the product as an orange solid.

MS (APCI, m/z, M+1): 337.0

NaH (60% in mineral oil, 3.55 g, 88 mmol) was added, in portions, to a solution of 2-fluoroethanol (5.19 g, 80 mmol) in 200 mL THF. The reaction was stirred for 60 minutes at room temperature. To the reaction was added 7-fluoro-6-nitro-4-(3-chloro-4-fluoroaniline)quinazoline (18.11 g, 54 mmol) as a solid, rinsing with THF. The reaction was heated to 65° C. for 26 hours. The reaction was cooled to room temperature and quenched with water. THF was removed in vacuo. The resulting residue was sonicated briefly in water then the solid collected by filtration. The solid was triturated with MeOH, filtered and dried in a 40° C. vacuum oven overnight to 12.63 g of the product. Additional product was obtained by concentrating the MeOH filtrate to dryness and chromatography eluting with 50% EtOAc/hex. The isolated material was triturated with MeOH (2×), filtered and dried. 3.90 g Total yield: 16.53 g, 81%

MS (APCI, m/z, M+1): 381.0

7-(2-fluoroethoxy)-6-nitro-4-(3-chloro-4-fluoroaniline) quinazoline (0.845 g, 2.2 mmol) in 50 mL THF was hydrogenated with Raney nickel (0.5 g) as the catalyst over 15 hours. The catalyst was filtered off and the filtrate was evaporated to give 0.77 g of product. (99%)

MS (APCI, m/z, M+1): 351.2

Methyl 4-bromocrotonate (85%, 20 mL, 144 mmol) was hydrolyzed with Ba(OH)₂ in EtOH/H₂O as described in J.Med.Chem. 2001, 44(17), 2729-2734.

MS (APCI, m/z, M−1): 163.0

To a solution of 4-bromocrotonic acid (4.17 g, 25 mmol) in CH₂Cl₂ (20 mL) was added oxalyl chloride (33 mL, 38 mmoL) and several drops of DMF. The reaction was stirred at room temperature for 1.5 hours. The solvent and excess reagent was removed in vacuo. The resulting residue was dissolved in 10 mL THF and added to a 0° C. mixture of 6-amino-7-(2-fluoroethoxy)-4-(3-chloro-4-fluoroaniline) quinazoline (5.28 g, 15 mmol) and triethylamine (5.2 mL, 37 mmol). The reaction was stirred at 0° C. for 1 hour. Water was added to the reaction and the THF removed in vacuo. The product was extracted into $CH_2Cl_2$ (400 mL). The organic layer was dried over $MgSO_4$, filtered and concentrated. The crude material was chromatographed on silica gel eluting with 0-4% $MeOH/CH_2Cl_2$. An isolated gold foam was isolated. Yield: 4.58 g, 61%

MS (APCI, m/z, M−1): 497.1

Piperidine (0.75 mL, 6.7 mmol) was added to a solution of the above compound (3.35 g, 6.7 mmol) and TEA (2.80 mL, 20 mmol) in 10 mL DMA at 0° C. The reaction was stirred at 0° C. for 17 hours. Water was added to the reaction until a precipitate was evident. The reaction was sonicated for 40 minutes and the liquid decanted. The residue was dissolved in $CH_2Cl_2$, dried over $MgSO_4$, filtered and concentrated. The material was chromatographed on silica gel eluting with 4-10% $MeOH/CH_2Cl_2$. The isolated residue was triturated with acetonitrile (2×) and collected by filtration. Impurity found: Michael addition of piperidine (2.2% in first trituration of acetonitrile). Additional material can be obtained from the acetonitrile filtrates.
Yield: 0.95 g, 27%
MS (APCI, m/z, M+1): 502.3

EXAMPLE 2

4-Piperidin-1-yl-but-2-enoic acid [4-(3-chloro-4-fluoro-phenylamino)-7-methoxy-quinazolin-6-yl]-amide (Synthetic Route No. 1)

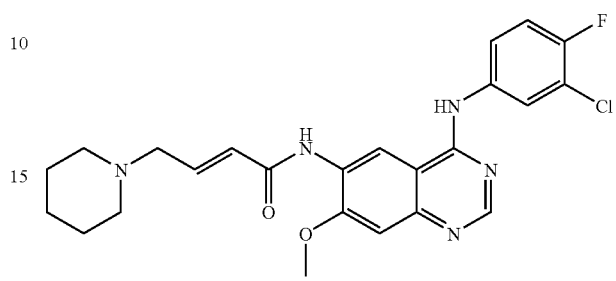

The title compound and other 7-methoxy analogs of this invention can be prepared as described in Example 1 by replacing the 2-fluoroethanol used in Example 1 with stoichiometric amount of methanol.

EXAMPLE 3

4-Piperidin-1-yl-but-2-enoic acid [4-(3-chloro-4-fluoro-phenylamino)-7-methoxy-quinazolin-6-yl]-amide (Synthetic Route No. 2)

An alternative synthetic route for compounds of this invention involves preparing the 6-position substituent chain as a Het-alkenoyl chloride as depicted in Scheme 2, below.

Scheme 2

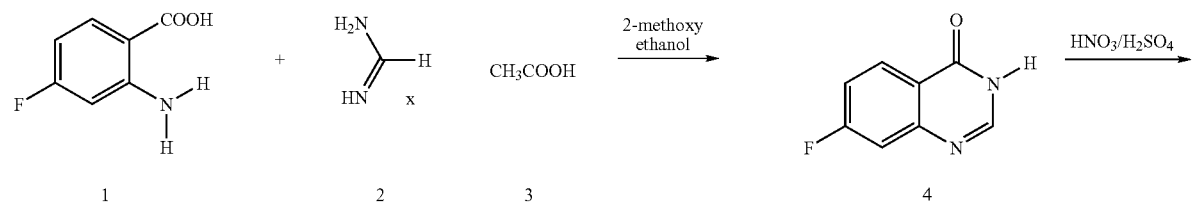

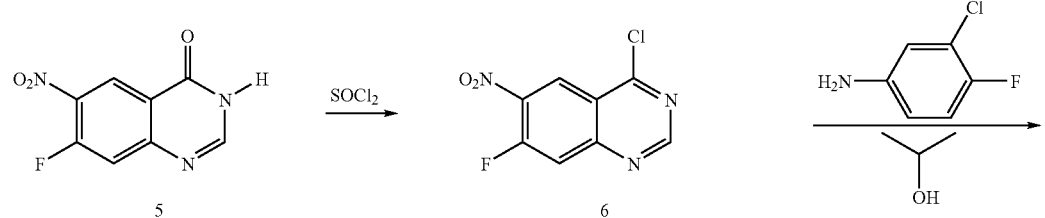

27
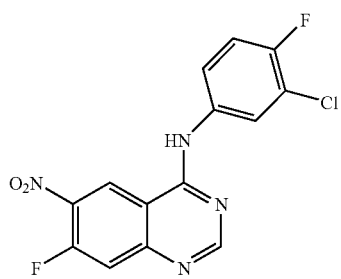
7
→ CH₃OH →
28
-continued
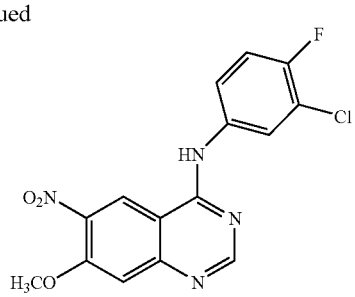
8
→ H₂ →
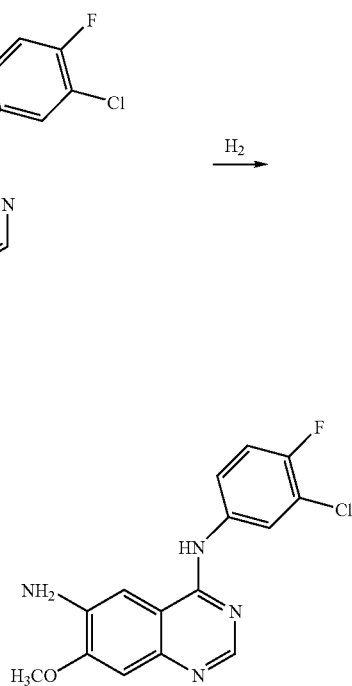
9
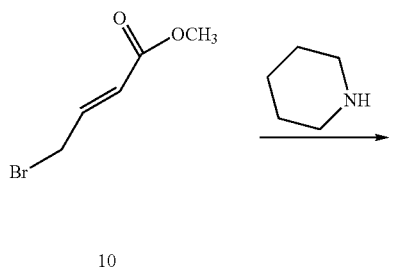
10
→ piperidine →
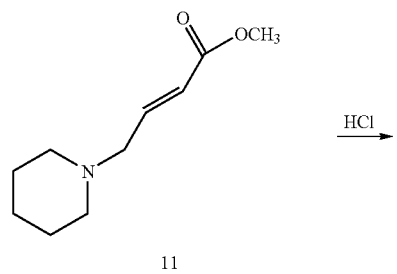
11
→ HCl →
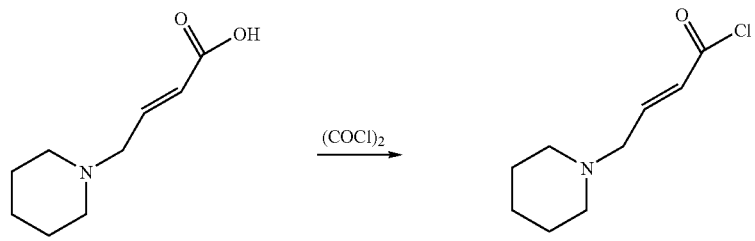
12 → (COCl)₂ → 13
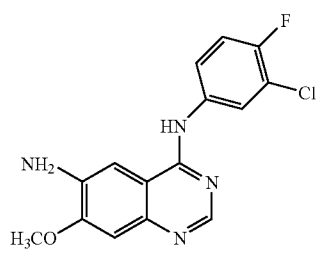
9
→ 13 →
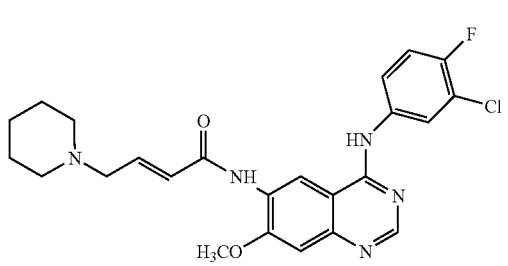
14

It will be understood that other compounds within this invention may be prepared using Het-butenoyl halide, Het-pentenoyl halide and Het-hexenoyl halide groups of the formula:

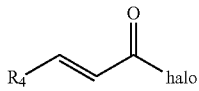

wherein $R_4$ is as described herein and halo represents F, Cl, Br or I, preferably Cl or Br. One specific group of these Het-alkenoyl halides includes those compounds in which halo is Cl or Br, $R_4$ is —$(CH_2)_m$-Het, m is an integer from 1 to 3, and Het is piperidine or the substituted piperidine moieties disclosed above.

EXAMPLE 4

4-Piperidin-1-yl-but-2-enoic acid [4-(3-chloro-4-fluoro-phenylamino)-7-methoxy-quinazolin-6-yl]-amide (Synthetic Route No. 3)

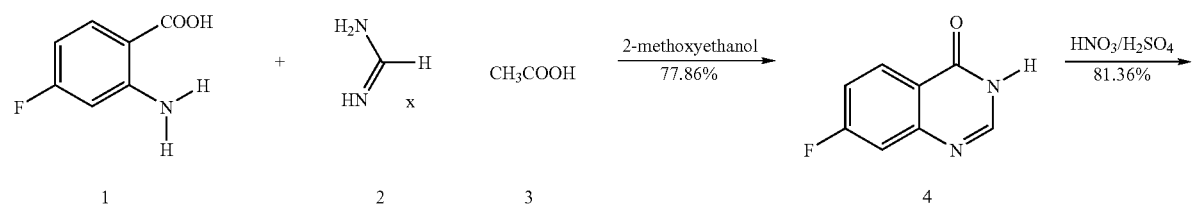

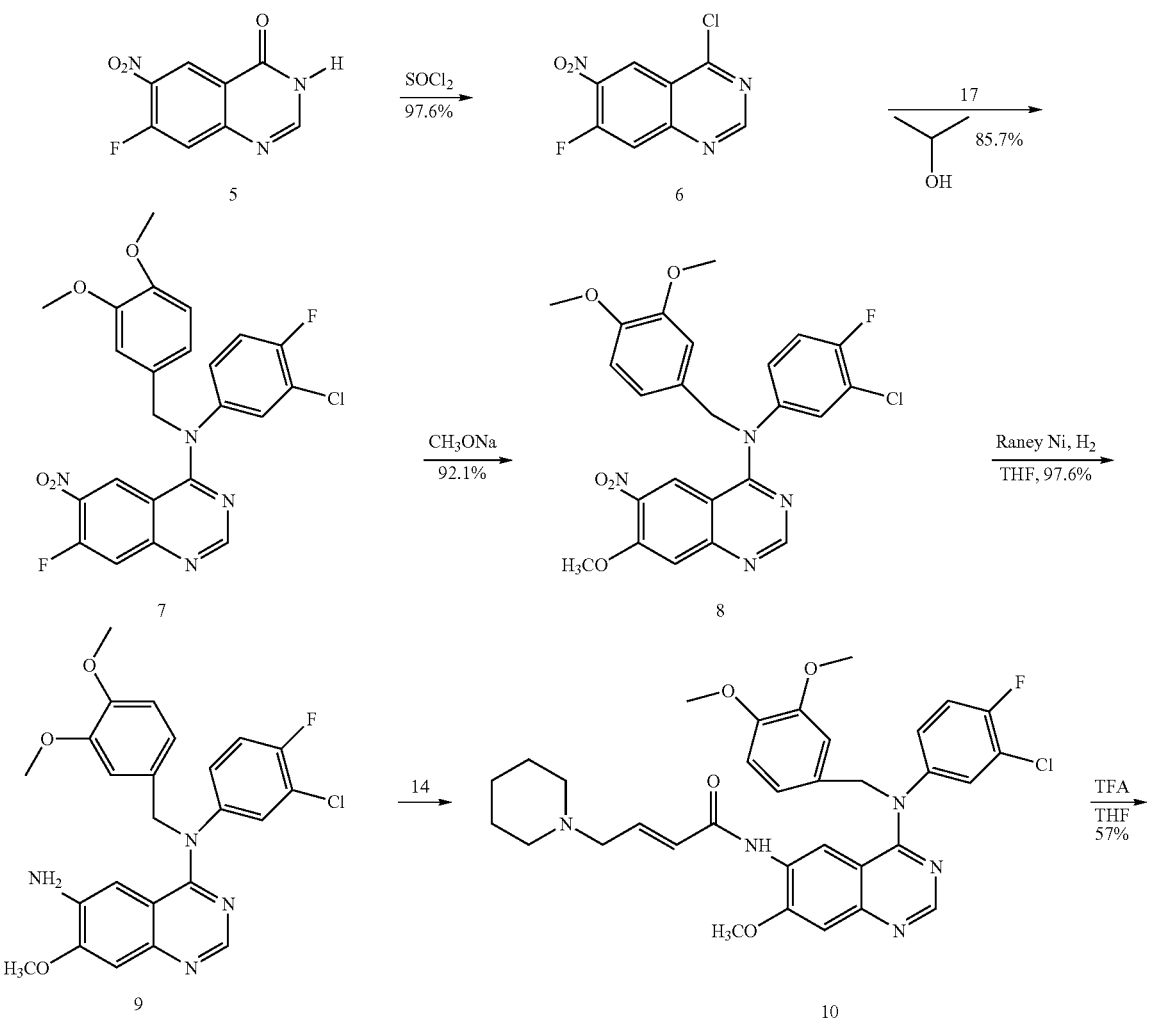

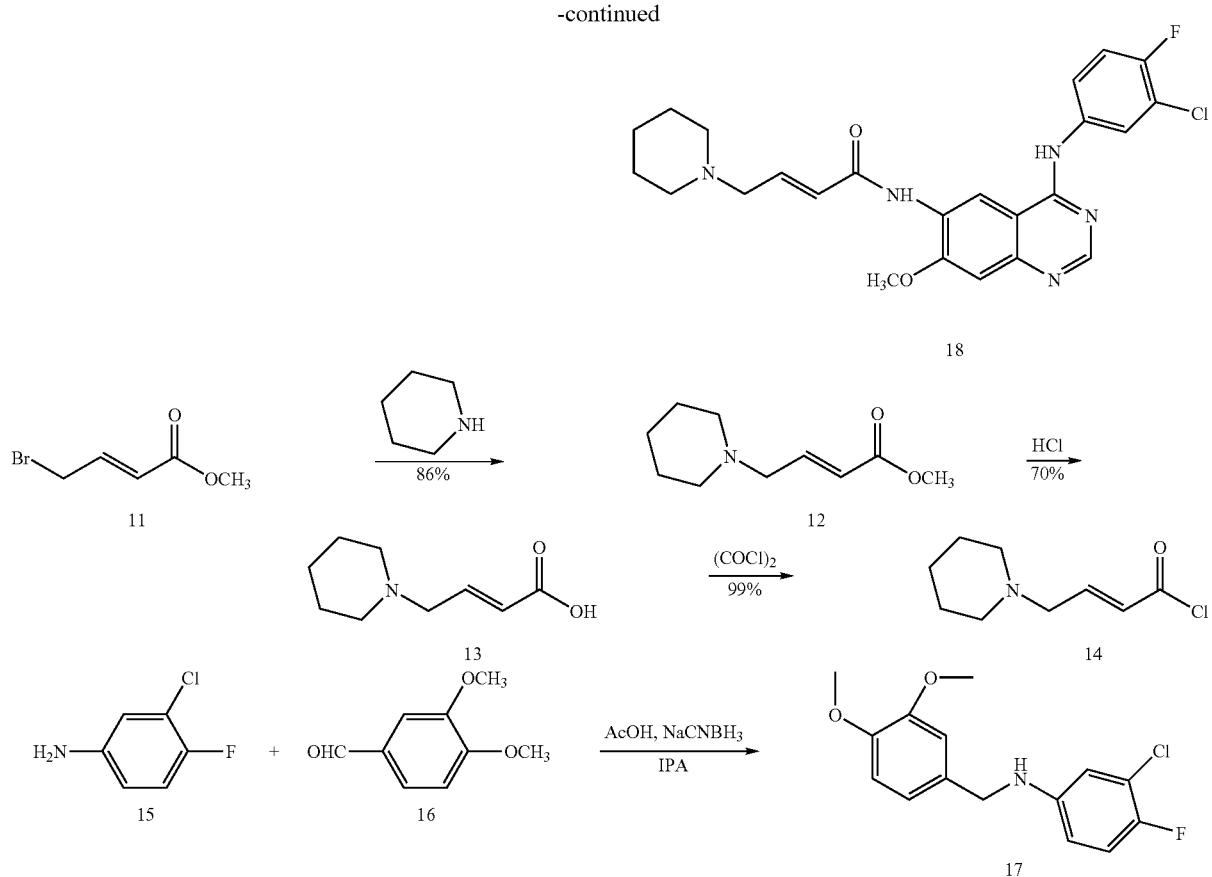

3-Chloro-4-fluoro-phenylamine 15 (50.31, 345.6 mmole) and 3,4-Dimethoxy-benzaldehyde 16 (57.43 g, 345.6 mmole) were mixed in 500 ml of IPA and cooled in an ice-water. The glacial acetic acid was added (20.76 g, 345.6 mole) and then sodium cyanoborohydride in one portion. The reaction was stirred at room temperature (RT) for 24 hrs. 250 mL of 10% NaOH was added dropwise at RT after the reaction was completed. The mixture was stirred for ½ hr. The slurry was then filtered and washed with IPA and dried in vacuo. The mass weight 88.75 g (17, 87%).

Compounds 6 (3 g, 13.18 mmole) and 17 (3.9 g, 13.18 mmole) were combined in $CH_3CN$ (25 mL) and heated for one hr. Mass spectroscopy indicated no starting material. Saturated $K_2CO_3$ was added and the reaction was extracted 3× with EtOAc. The organic layers were combined, washed with brine and concentrated in vacuo to give 6.48 g of 7 (78.4%).

Compound 7 (72.76 g, 149.4 mmole) was added to a cool solution of NaOMe in 1.5 L of dry MeOH under $N_2$. The cooling bath was removed and the mixture was heated to reflux and stirred for 1 hr. The reaction was cooled to room temperature and quenched with water until the product precipitated out. The solid was filtered and washed with water and hexanes. The product was slurred in refluxing EtOAc and filtered hot to provide 68.75 g of yellow soled 8 (73%).

Compound 8 (63.62 g, 127.5 mole) was hydrogenated using Raney/Ni as catalyst to obtain 43.82 g of 9 (100%). Oxalyl chloride (6.5 g, 51.18 mmole) was added slowly to a suspension of 13 (10.5 g, 51.2 mmole) in 200 ml of dichloromethane containing 8 drops of DMF, after the reaction become homogeneous, the solvent was removed and the residual light yellow solid was slurred in 200 ml of DMAC and 9 (20 g, 42.65 mmole) was added gradually as a solid. The reaction was stirred for 15 min. and poured slowly into 1N NaOH. The mixture was extrated 3× EtOAc. The combined organic layers were washed with brine, filtered and concentrated in vacuo to obtain 28.4 g (100%) 10.

Compound 10(13.07 g, 21.08 mmole) was dissolved in trifluoroacetic acid (TFA) (74 g, 649 mmole) and heated to 30° C. for 24 hrs. The reaction was cooled to RT and poured gradually into a cooled 1 N NaO H-brine solution. Precipitate formed and was filtered and washed with 3X water then dried. The precipitate was recrystallized from toluene to obtain pure 4-Piperidin-1-vl-but-2-enoic acid [4-(3-chloro-4-fluoro-phenylamino) -7-methoxv-puinazolin-6-yl]-amide (9.90 g, 89%).

From the example above, it will be understood that this invention includes useful intermediate compounds of the formula:

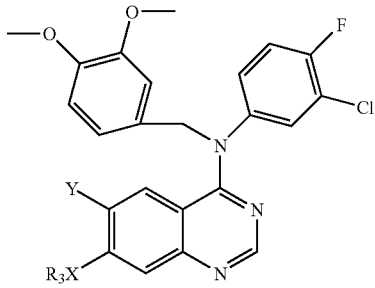

wherein Y is NH₂, NO₂ or the moiety R₄—(CH₂)ₘ—CH═CH—C(O)—NH₂—; and m is integer from 1 to 3;

R₃ is selected from:
a) $C_1$-$C_3$ straight or branched alkyl, optionally substituted by halogen; or
b) —(CH₂)ₙ-morpholino, —(CH₂)ₙ-piperidine, —(CH₂)ₙ-piperazine, —(CH₂)ₙ-piperazine-N($C_1$-$C_3$ alkyl), —(CH₂)ₙ-pyrrolidine, or —(CH₂)ₙ-imidazole;

n is an integer from 1 to 4;

R₄ is —(CH₂)ₘ-Het;

Het is a heterocyclic moiety selected from the group of morpholine, piperidine, piperazine, piperazine-N($C_1$-$C_3$ alkyl), imidazole, pyrrolidine, azepane, 3,4-dihydro-2H-pyridine, or 3,6-dihydro-2H-pyridine, wherein each heterocyclic moiety is optionally substituted by from 1 to 3 groups selected from $C_1$-$C_3$ alkyl, halogen, OH, NH₂, NH($C_1$-$C_3$ alkyl) or N ($C_1$-$C_3$ alkyl)₂;

m is an integer from 1 to 3; and

X is O, S or NH.

EXAMPLE 5

4-Piperidin-1-yl-but-2-enoic acid [4-(3-chloro-4-fluoro-phenylamino)-7-methoxy-quinazolin-6-yl]-amide (Synthetic Route No. 4)

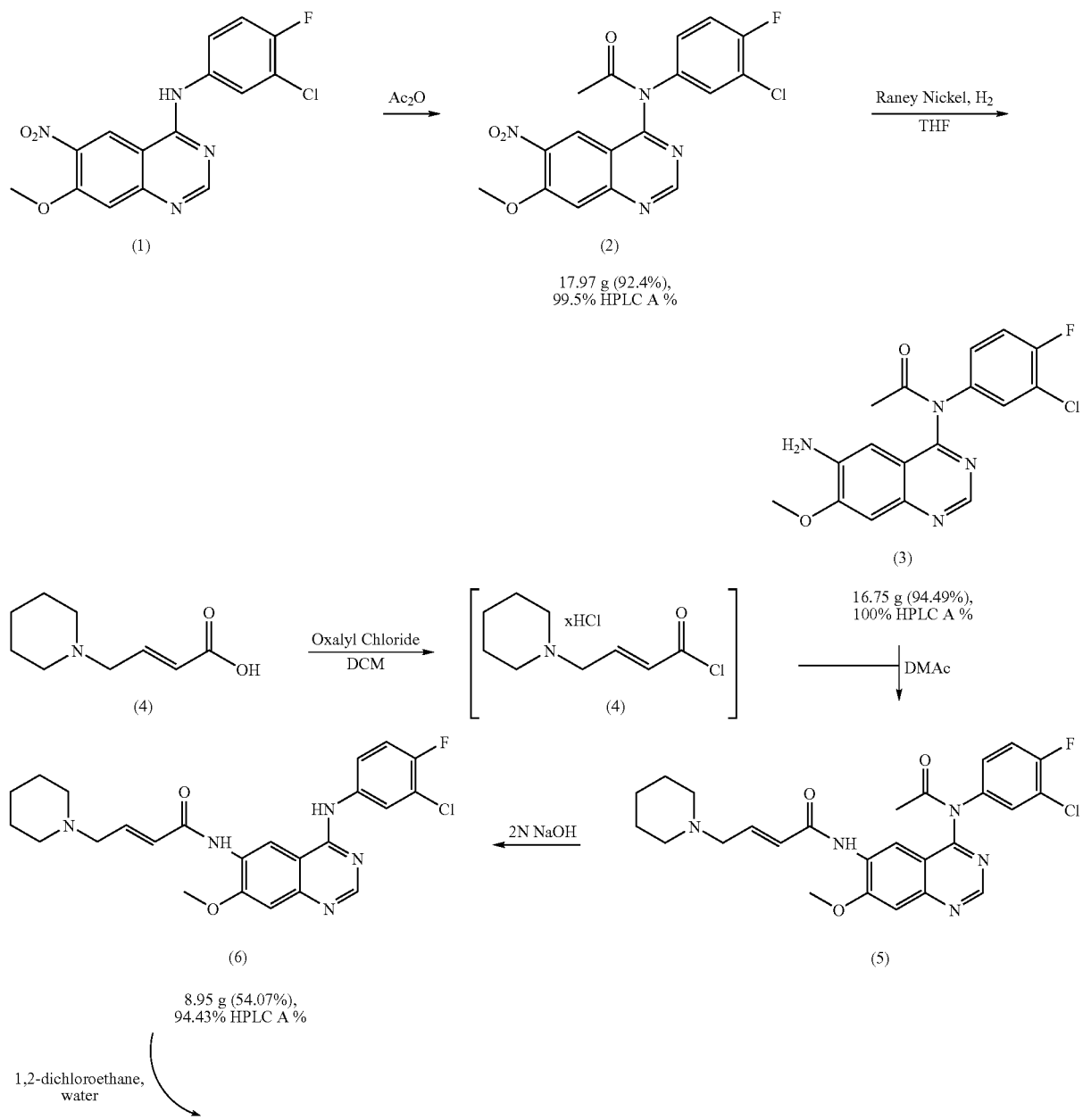

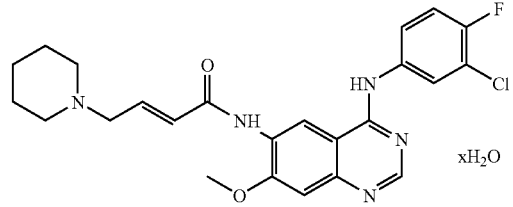

(3-Chloro-4-fluoro-phenyl-(7-methoxy-6-nitro-quinazoline-4-yl)-amine (1) (1 7.26 g, 0.0495 mmol) was slurried in 350 ml acetic anhydride under nitrogen and warmed and maintained at 90° C. for 24 hrs and cooled gradually to RT. Pale colored slurry exists. Cooled to 0° C. for 1 hr. The solids were filtered and the flask and cake were washed with 2×50 ml IPA. The product, N-(3-Chloro-4-fluoro-phenyl)-N-(7-methoxy-6-nitro-quinazoline-4-yl)-acetamide (2), was dried in vacuum oven at 60° C. for 24 hrs. Mass: 17.97 g (92.4%). HPLC: 99.45%, rt=13.705 min.

Raney Ni (5.0 g) was slurried in MeOH, followed by THF to remove water. N-(3-Chloro-4-fluoro-phenyl)-N-(7-methoxy-6-nitro-quinazoline-4-yl)-acetamide (2) (19.2 g, 49 mmol) was slurried in THF (500 ml) and charged to a reactor. The reaction was heated to 60° C. and pressurized with hydrogen to 60 psi. After almost 17 hrs, an additional 10.0 g of the catalyst was charged and the reaction was complete by 38 hrs. Filter reaction and wash with THF. The solids were concentrated on rotavap and the solvent was exchanged to hexanes. A pale yellow solid precipitated upon addition of hexanes. The solvent was removed under vacuum to distill any remaining THF. Filtered and washed with copious amounts of hexanes. The product, N-(6-Amino-7-methoxy-quinazolin-4-yl)-N-(3-chloro-4-fluoro-phenyl)-acetamide (3), was dried in vacuum oven at 70° C. for 24 hours. Mass is 16.75 g (94.49%). HPLC: tm (100%).

Oxyalyl chloride was added to a solution of DMF (60 mg), 4-piperidin-1-yl-but-2-enoic acid in 40 ml DCM at room temperature and the reaction was stirred for one hour. The solvent was evaporated under vacuum and the resulting solid slurried in 150 ml DMAC. The N-(6-amino-7-methoxy-quinazolin-4-yl)-N-(3-chloro-4-fluoro-phenyl)-acetamide (3) was added to the reaction mixture as a solid. The reaction was completed after 45 minutes. The mixture was then added dropwise to 300 ml 2N NaOH and the aqueous layer was extracted into EtOAc. The combined organic layer was concentrated to 100 ml and stirred for 2 days at room temperature. 300 ml ethyl ether and 100 ml of 2N NaOH were added and the solid that precipitated out was collected by filtration. The final product was recrystallized from ethylene chloride to obtain 5.5 g pure product.

As noted above, the Raney nickel catalyst may be treated prior to use with an alcohol, such as methanol or ethanol, then washed with THF prior to use. Additional catalysts for use with this reaction include platinum on carbon or palladium on carbon catalysts, preferably in the presence of 1-4 equivalents of acetic acid.

It will be understood that the removal of the acetyl group on compound (5) to provide compound (6), above, may be accomplished by methods known in the art, including both basic and acidic conditions. Removal under acidic conditions may be accomplished utilizing, among other acids known in the art, acetic acid or methanesulfonic acid.

Within the scope of this invention are useful intermediate compounds of the formula:

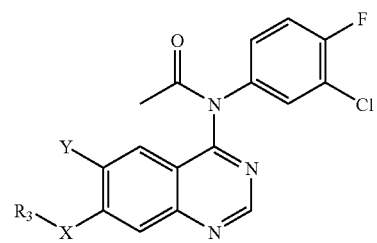

wherein Y is $NH_2$, $NO_2$ or the moiety $R_4$—$(CH_2)_m$—CH=CH—C(O)—$NH_2$—; and m is an integer from 1 to 3;

$R_3$ is selected from:
a) $C_1$-$C_3$ straight or branched alkyl, optionally substituted by halogen; or
b) —$(CH_2)_n$-morpholino, —$(CH_2)_n$-piperidine, —$(CH_2)_n$-piperazine, —$(CH_2)_n$-piperazine-N($C_1$-$C_3$ alkyl), —$(CH_2)_n$-pyrrolidine, or —$(CH_2)_n$-imidazole;

n is an integer from 1 to 4;

$R_4$ is —$(CH_2)_m$-Het;

Het is a heterocyclic moiety selected from the group of morpholine, piperidine, piperazine, piperazine-N($C_1$-$C_3$ alkyl), imidazole, pyrrolidine, azepane, 3,4-dihydro-2H-pyridine, or 3,6-dihydro-2H-pyridine, wherein each heterocyclic moiety is optionally substituted by from 1 to 3 groups selected from $C_1$-$C_3$ alkyl, halogen, OH, $NH_2$, NH($C_1$-$C_3$ alkyl) or N ($C_1$-$C_3$ alkyl)$_2$;

m is an integer from 1 to 3; and

X is O, S or NH.

Examples of these include N-(3-chloro-4-fluoro-phenyl)-N-(7-methoxy-6-nitro-quinazolin-4-yl)-acetamide, N-(6-amino-7-methoxy-quinazolin-4-yl)-N-(3-chloro-4-fluoro-phenyl)-acetamide and N-{4-[acetyl-(3-chloro-4-fluoro-phenyl)-amino]-7-methoxy-quinazolin-6-yl}-3-piperidin-1-yl-acrylamide.

EXAMPLE 6

4-Piperidin-1-yl-but-2-enoic acid [4-(3-chloro-4-fluoro-phenylamino)-7-(2,2-difluoroethoxy)-Quinazolin-6-yl]-amide

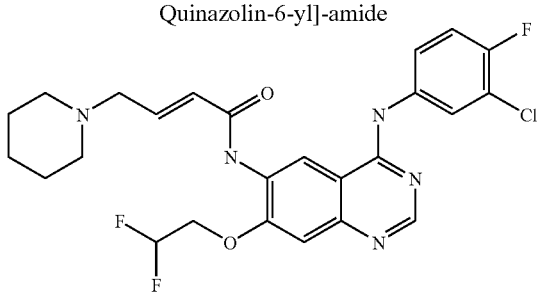

0.6 g 60% NaH was added in portions to a solution of 1.23 g 2,2-difluoroethanol in 20 ml THF and stirred at room temperature for 15 minutes. 2.02 g (3-Chloro-4-fluoro-phenyl)-(7-fluoro-6-nitro-quinazoline-4-yl)-amine was added as a solid and the mixture was heated to 65° C. for 1 hour, then cooled to room temperature. Water was added and the THF was removed under vacuum. The mixture was sonicated and the resulting solids collected by filtration and dried under vacuum overnight to give 2.93 g of crude (3-Chloro-4-fluoro-phenyl)-[7-(2,2-difluoro-ethoxy)-6-nitro-quinazolin-4-yl]-amine.

The crude (3-Chloro-4-fluoro-phenyl )-[7-(2,2-difluoro-ethoxy)-6-nitro-quinazolin-4-yl]-amine was dissolved in THF and reduced using Raney nickel catalyst to yield $N^4$-(3-Chloro-4-fluoro-phenyl)-7-(2,2-difluoro-ethoxy)-quinazoline-4,6-diamine.

0.45 g Bromo-but-2-enoic acid was dissolved in 10 ml $CH_2Cl_2$ along with 2 drops DMF. 0.47 ml oxalyl chloride was added at room temperature and stirred overnight. The mixture was evaporated to dryness to yield 4-Bromo-but-2-enoyl chloride.

0.5 g $N^4$-(3-Chloro-4-fluoro-phenyl)-7-(2,2-difluoro-ethoxy)-quinazoline4,6-diamine was dissolved in 10 ml THF and 1.2 ml N,N-Diisopropyl-ethylamine (DIEA) and 0.48 g 4-Bromo-but-2-enoyl chloride were added and the mixture was stirred at room temperature for 2 hours. 0.27 ml piperidine was added and stirred at room temperature overnight. An additional 0.7 ml piperidine was added and the mixture heated to 70° C. After 3 hours the reaction mixture was poured into water, the solids were extracted with ethyl acetate, washed with water and brine, dried over $NaSO_4$ and flash chromatographed under 0-4% methanol in chloroform to yield 0.2 g 4-Piperidine-1-yl-but-2-enoic acid [4-(3-chloro-4-fluoro-phenylamino)-7-(2,2-difluoro-ethoxy)-quinazolin-6-yl]-amide.

MS $(M+H)^+$ @520.

EXAMPLE 7

4-Piperidin-1-yl-but-2-enoic acid [4-(3-chloro-4-fluoro-phenylamino)-7-(3-morpholin-4-yl-propoxy)-quinazolin-6-yl]-amide

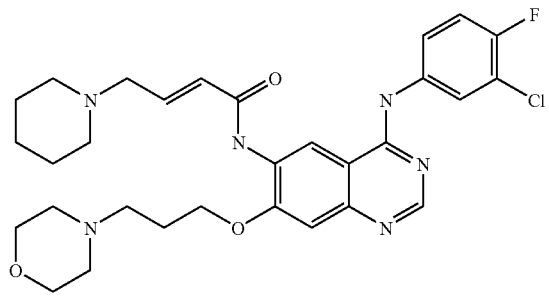

Step 1: 4-Piperidin-1-yl-but-2-enoic acid methyl ester

Methyl 4-bromocrotonate (2 g, 11.2 mmol) was dissolved in dichloromethane (20 mL) and cooled to 0° C. Piperidine (1.11 mL, 11.2 mmol) was added slowly. The mixture was stirred at 0° C. for 1 hour. The solvent was removed in vacuo. The crude material was used as is. MS m/z 184 (M+1).

Step 2: 4-Piperidin-1-yl-but-2-enoic acid —HCl

4-Piperidin-1-yl-but-2-enoic acid methyl ester (2.05 g, 11.2 mmol) and concentrated hydrochloric acid (10 mL) were combined in dioxanes (30 mL) and heated to reflux overnight. The mixture was concentrated in vacuo. The residue was crystallized from IPA to yield the desired product (390 mg, 17%). 400 MHz $^1$H NMR (DMSO-$d_6$) δ 6.80 (dt, 1H, J=15.6, 7.1 Hz), 6.14 (d, 1H, J=15.6 Hz), 3.85 (d, 1H, J=7.1 Hz), 2.89 (m, 4H), 1.54 (m, 6H), MS m/z 170 (M+1).

Step 3: 4-Piperidin-1-yl-but-2-enoyl chloride

The HCl salt of 4-Piperidin-1-yl-but-2-enoic acid (250 mg, 1.48 mmol) was dissolved in dichloromethane (15 mL). Dimethylformamide (3 drops) was added. Oxalyl chloride (155 μL, 1.77 mmol) was added slowly and the reaction was stirred at room temperature for 1 hour. The mixture was concentrated under reduced pressure and the residue was used as is.

Step 4: 4-Piperidin-1-yl-but-2-enoic acid [4-(3-chloro-4-fluoro-phenylamino)-7-(3-morpholin-4-yl-propoxy)-quinazolin-6-yl]-amide N*4*-(3-Chloro-4-fluoro-phenyl)-7-(3-morpholin-4-yl-propoxy)-quinazoline-4,6-diamine (510 mg, 1.18 mmol) and DIPEA (620 μL, 3.55 mmol) were combined in tetrahydrofuran (10 mL) and cooled to 0° C. 4-Piperidin-1-yl-but-2-enoyl chloride (278 mg, 1.48 mmol) was added and the reaction stirred at 0° C. for 2 hours. The mixture was quenched with ethyl acetate, dried with $MgSO_4$ and concentrated. The residue was purified using chromatography on silica eluting with 15%-20% MeOH in $CH_2Cl_2$ to yield the desired product (20 mg). 400 MHz $^1$H NMR (DMSO-d6) δ 8.82 (s, 1H), 8.50 (s, 1H), 8.11 (dd, 1H, J=6.9, 2.6 Hz), 7.77 (m, 1H), 7.40 (t,1H, J=9.0 Hz), 7.25 (s,1H), 6.76 (m,1H), 6.53 (m, 1H), 4.23 (t, 2H, J=6.0 Hz), 3.55 (m, 4H), 3.08 (m, 2H), 2.40 (m, 10H), 1.96 (m, 2H), 1.29 (m, 6H). MS m/z 584 (M+1).

EXAMPLE 8

4-(3-Fluoro-piperidin-1-yl)-but-2-enoic acid [4-(3-chloro-4-fluoro-phenylamino)-7-methoxy-quinazolin-6-yl]-amide

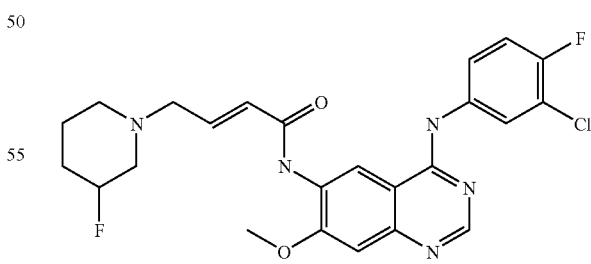

99 mg 3-Fluoro-piperidine hydrochloride, 300 mg 4-Chloro-but-2-enoic acid [4-(3-chloro-4-fluoro-phenylamino)-7-methoxy-quinazolin-6-yl]-amide and 0.37 ml of DIEA were dissolved in 5 ml THF stirred at 70° C. overnight. The mixture was then diluted with ethyl acetate, washed with water and brine and dried over $Na_2SO_4$. The resulting solids were flash chromatographed with 0-4% methanol in chloroform to give 275 mg of 4-(3-Fluoro-piperidin-1-yl)-but-2-enoic acid [4-(3-chloro-4-fluoro-phenylamino)-7-methoxy-quinazolin-6-yl]-amide.

(M+H)+ @ 488.

EXAMPLE 9

4-(4-Fluoro-piperidin-1-yl)-but-2-enoic acid [4-(3-chloro4-fluoro-phenylamino)-7-methoxy-quinazolin-6-yl]-amide

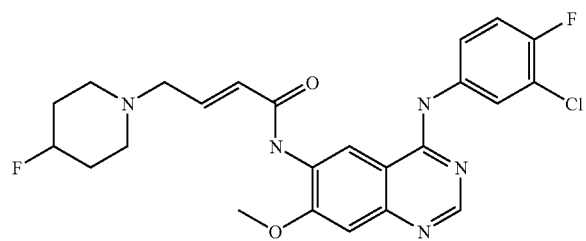

131 mg of 4-Fluoro-piperidine hydrobromide was added to 300 mg of 4-Chloro-but-2-enoic acid [4-(3-chloro-4-fluoro-phenylamino)-7-methoxy-quinazolin-6-yl]-amide and 0.37 ml of DIEA were dissolved in 5 ml THF stirred at 70° C. overnight. The mixture was then diluted with ethyl acetate, washed with water and brine and dried over Na$_2$SO$_4$. The resulting solids were flash chromatographed with 04% methanol in chloroform to give 189.4 mg of 4-(4-Fluoro-piperidin-1-yl)-but-2-enoic acid [4-(3-chloro-4-fluoro-phenylamino)-7-methoxy-quinazolin-6-yl]-amide.

(M+H)+ @ 488.

EXAMPLE 10

4-Azepan-1-yl-but-2-enoic acid [4-(3-chloro-4-fluoro-phenylamino)-7-methoxy-quinazolin-6-yl]-amide

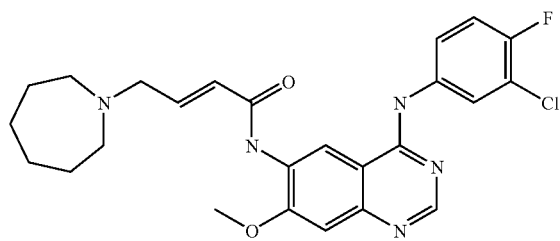

(3-Chloro-4-fluoro-phenyl)-(7-fluoro-6-nitro-quinazolin-4-yl)-amine was suspended in 100 ml methanol and 2 ml 50% NaOH in water was added and the mixture was heated at 70° C. for 2 hours. The mixture was then poured into water and stirred vigorously for 30 minutes, then filtered and washed with water and dried under vacuum at 60° C. overnight to give 7.2 g of (3-Chloro-4-fluoro-phenyl)-(7-methoxy-6-nitro-quinazolin-4-yl)-amine.

7.1 g of (3-Chloro-4-fluoro-phenyl)-(7-methoxy-6-nitro-quinazolin-4-yl)-amine was reduced using Raney nickel catalyst in THF, then filtered and evaporated to give 6.4 g N$^4$-(3-Chloro-4-fluoro-phenyl)-7-methoxy-quinazoline-4,6-diamine (99% yield). This product was reacted with 4-Chloro-but-2-enoyl chloride as described in Scheme 1 to provide 4-Chloro-but-2-enoic acid [4-(3-chloro-4-fluoro-phenylamino)-7-methoxy-quinazolin-6-yl]-amide.

300 g of 4-Chloro-but-2-enoic acid [4-(3-chloro4-fluoro-phenylamino)-7-methoxy-quinazolin-6-yl]-amide and 78 mg azepane were dissolved in 5 ml THF and purged with nitrogen. 0.25 ml DIEA was added and the mixture was stirred at 70° C. for 2 days. The mixture was then diluted with 20 ml ethyl acetate, washed with water and brine and dried over Na$_2$SO$_4$. The resulting solids were flash chromatographed with 0-4% methanol in chloroform. The product was dissolved in CH$_2$Cl$_2$ and treated with excess HCl and ether, then evaporated to dryness to give 115 mg of 4-Azepan-1-yl-but-2-enoic acid [4-(3-chloro-4-fluoro-phenylamino)-7-methoxy-quinazolin-6-yl]-amide (33% yield).

(M+H)+ @484.

EXAMPLE 11

ELISA-based erbB Kinase Assay

ErbB1, erbB2 and erbB4 cytoplasmic fusion proteins were made by cloning the erbB1 sequence (Met-668 to Ala1211), erbB2 (Ile-675 to Val-1256) and erbB4 sequence (Gly-259 to Gly-690) into the baculoviral vector pFastBac using Polymerase Chain Reaction (PCR). Proteins were expressed in Baculovirus-infected Sf9 insect cells as Glutathione S-Transferase (GST) fusion proteins. The proteins were purified by affinity chromatography using glutathione sepharose beads.

Inhibition of erbB tyrosine kinase activity was assessed using an ELISA-based receptor tyrosine kinase assay. Kinase reactions (50 mM HEPES, pH 7.4, 125 mM NaCl, 10 mM MgCl$_2$, 100 μM sodium orthovanadate, 2 mM dithiothreitol, 20 uM ATP, test compound or vehicle control and 1-5 nM GST-erbB per 50 uL reaction) were run in 96-well plates coated with 0.25 mg/ml poly-Glu-Tyr (Sigma). The reactions were incubated for 6 minutes at room temperature while shaking. Kinase reactions were stopped by removal of reaction mixture, then wells were washed with wash buffer comprising 3% Bovine Serum Albumin and 0.1% Tween 20 in Phosphate Buffered Saline (PBS). Phosphorylated tyrosine residues were detected by adding 0.2 μg/ml anti-phosphotyrosine antibody (Oncogene Ab-4; 50 μL/well) coupled to Horse Radish Peroxidase (HRP) for 25 minutes while shaking at room temperature. The antibody was removed, and plates were washed (3% BSA and 0.1% Tween 20 in PBS). HRP substrate 3,3',5,5'-tetramethylbenzidene (SureBlueTMB, Kirkegaard & Perry Labs) was added (50 μL per well) and incubated for 10-20 minutes while shaking at room temperature. The TMB reaction was stopped with the addition of 50 μL stop solution (0.09 N H$_2$SO$_4$) The signal was quantified by measuring absorbance at 450 nm. IC$_{50}$ values were determined for test compounds using Microsoft Excel.

| Compound | | | |
|---|---|---|---|
| | ErbB1 IC$_{50}$ (nM) | ErbB2 IC$_{50}$ (nM) | ErbB4 IC$_{50}$ (nM) |
| Example No. 1 | 6.44 | | 77.5 |
| Example No. 2 | 6.9 | 16.7 | 83.67 |
| Example No. 6 | 9.87 | 244.39 | 154 |
| Example No. 7 | 11.35 | 84.05 | 61.5 |
| Example No. 8 | 45.34 | 212.11 | 233.8 |
| Example No. 9 | 18.08 | 247.12 | 147 |
| Example No. 10 | 12.13 | 85.98 | 41.33 |

What is claimed:
1. A compound of the formula:

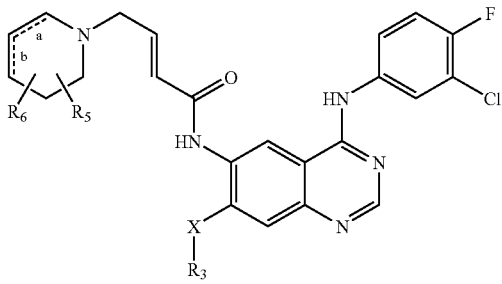

or a pharmaceutically acceptable salt thereof, wherein:
$R_3$ is $C_1$-$C_3$ straight or branched alkyl, optionally substituted by one or more halogens;
$R_5$ and $R_6$ are each independently selected from H, $C_1$-$C_3$ alkyl, F, Br, I and Cl;
X O, S or NH; and
the dashed lines designated a and b each indicate an optional double bond, with the proviso that the optional double bond a and the optional double bond b may not both exist in one compound.

2. A compound according to claim 1, wherein X is O and $R_3$ is $C_1$-$C_3$ straight or branched alkyl optionally substituted by from 1 to 3 halogen atoms, or a pharmaceutically acceptable salt thereof.

3. A compound, which is selected from the following group of compounds:
   4-Piperidin-1-yl-but-2-enoic acid [4(3-chloro-4-fluoro-phenylamino)-7-methoxy-quinazolin-6-yl]-amide;
   4-Piperidin-1-yl-but-2-enoic acid [4(3-chloro-4-fluoro-phenylamino)-7-methylsulfanyl-quinazolin-6-yl]-amide;
   4-Piperidin-1-yl-but-2-enoic acid [4(3-chloro-4-fluoro-phenylamino)-7-methylamino-quinazolin-6-yl]-amide;
   4-Piperidin-1-yl-but-2-enoic acid [4(3-chloro-4-fluoro-phenylamino)-7-isopropoxy-quinazolin-6-yl]-amide;
   4-Piperidin-1-yl-but-2-enoic acid [4(3-bromo-phenylamino)-7-methoxy-quinazolin-6-yl]-amide;
   4-Piperidin-1-yl-but-2-enoic acid [4(3-chloro-4-fluoro-phenylamino)-7-ethoxy-quinazolin-6-yl]-amide;
   4-Piperidin-1-yl-but-2-enoic acid [4(3-chloro-4-fluoro-phenylamino)-7-propoxy-quinazolin-6-yl]-amide;
   4-(4-Fluoro-piperidin-1-yl)-but-2-enoic acid [4-(3-chloro-4-fluoro-phenylamino)-7-methoxy-quinazolin-6-yl]-amide;
   4-(3-Fluoro-piperidin-1-yl)-but-2-enoic acid [4-(3-chloro-4-fluoro-phenylamino)-7-methoxy-quinazolin-6-yl]-amide;
   4-(2-Fluoro-piperidin-1-yl)-but-2-enoic acid [4-(3-chloro-4-fluoro-phenylamino)-7-methoxy-quinazolin-6-yl]-amide;
   4-Piperidin-1-yl-but-2-enoic acid [4(3-chloro-4-fluoro-phenylamino)-7-trifluoromethoxy-quinazolin-6-yl]-amide;
   4-Piperidin-1-yl-but-2-enoic acid [4(3-chloro-4-fluoro-phenylamino)-7-fluoromethoxy-quinazolin-6-yl]-amide;
   4-Piperidin-1-yl-but-2-enoic acid [4(3-chloro-4-fluoro-phenylamino)-7-fluoroethoxy-quinazolin-6-yl]-amide;
   4-Piperidin-1-yl-but-2-enoic acid [4(3-chloro-4-fluoro-phenylamino)-7-(2-fluoro-ethylsulfanyl)-quinazolin-6-yl]-amide;
   4-Piperidin-1-yl-but-2-enoic acid [4(3-chloro-4-fluoro-phenylamino)-7-trifluoroethoxy-quinazolin-6-yl]-amide;
   4-Piperidin-1-yl-but-2-enoic acid [4(3-chloro-4-fluoro-phenylamino)-7-difluoroethoxy-quinazolin-6-yl]-amide;
   4-(3,4-Dihydro-2H-pyridin-1-yl)-but-2-enoic acid [4(3-chloro-4-fluoro-phenylamino)-7-methoxy-quinazolin-6-yl]amide;
   4-(3,6-Dihydro-2H-pyridin-1-yl)-but-2-enoic acid [4(3-chloro-4-fluoro-phenylamino)-7-methoxy-quinazolin-6-yl]amide;
   4-(3,4-Dihydro-2H-pyridin-1-yl)-but-2-enoic acid [4(3-chloro-4-fluoro-phenylamino)-7-ethoxy-quinazolin-6-yl]amide;
   4-(3,4-Dihydro-2H-pyridin-1-yl)-but-2-enoic acid [4(3-chloro-4-fluoro-phenylamino)-7-fluoroethoxy-quinazolin-6-yl]amide;
   4-(3,6-Dihydro-2H-pyridin-1-yl)-but-2-enoic acid [4(3-chloro-4-fluoro-phenylamino)-7-fluoroethoxy-quinazolin-6-yl]amide; and
   a pharmaceutically acceptable salt of any of the aforementioned compounds.

4. A pharmaceutical composition comprising:
   a pharmaceutically effective amount of a compound as defined in claim 1, or a pharmaceutically acceptable salt thereof; and
   a pharmaceutically acceptable carrier.

5. A pharmaceutical composition comprising:
   a pharmaceutically effective amount of 4-Piperidin-1-yl-but-2-enoic acid [4-(3-chloro-4-fluoro-phenylamino)-7-methoxy-quinazolin-6-yl]-amide or a pharmaceutically acceptable salt thereof, and
   a pharmaceutically acceptable carrier.

6. A compound which is 4-Piperidin-1-yl-but-2-enoic acid [4-(3-chloro-4-fluoro-phenylamino)-7-methoxy-quinazolin-6-yl]-amide or a pharmaceutically acceptable salt thereof.

7. A compound which is selected from the following group of compounds:
   4-Morpholin-4-yl-but-2-enoic acid [4(3-chloro-4-fluoro-phenylamino)-7-methoxy-quinazolin-6-yl]-amide;
   4-Azepan-1-yl-but-2-enoic acid [4-(3-chloro-4-fluoro-phenylamino)-7-methoxy-quinazolin-6-yl]-amide;
   4-Piperidin-1-yl-but-2-enoic acid [4(3-chloro-4-fluoro-phenylamino)-7-(3-morpholin-4-yl-propoxy)-quinazolin-6-yl]-amide;
   4-Piperidin-1-yl-but-2-enoic acid [4(3-chloro-4-fluoro-phenylamino)-7-(2-piperidin-1-yl-ethoxy)-quinazolin-6-yl]-amide;
   4-Piperazin-1-yl-but-2-enoic acid [4(3-chloro-4-fluoro-phenylamino)-7-methoxy-quinazolin-6-yl]amide;
   4-(4-Methyl-piperazin-1-yl)-but-2-enoic acid [4(3-chloro-4-fluoro-phenylamino)-7-methoxy-quinazolin-6-yl]amide;
   4-Imidazol-1-yl-but-2-enoic acid [4(3-chloro-4-fluoro-phenylamino)-7-methoxy-quinazolin-6-yl]amide;
   4-Pyrrolidin-1-yl-but-2-enoic acid [4(3-chloro-4-fluoro-phenylamino)-7-methoxy-quinazolin-6-yl]amide;
   5-Piperidin-1-yl-pent-2-enoic acid [4(3-chloro-4-fluoro-phenylamino)-7-methoxy-quinazolin-6-yl]-amide;
   5-Piperidin-1-yl-pent-2-enoic acid [4(3-chloro-4-fluoro-phenylamino)-7-methylsulfanyl-quinazolin-6-yl]-amide;
   5-Piperidin--yl-pent-2-enoic acid [4(3-chloro-4-fluoro-phenylamino)-7-methylamino-quinazolin-6-yl]-amide;
   5-Piperidin-1-yl-pent-2-enoic acid [4(3-chloro-4-fluoro-phenylamino)-7-isopropoxy-quinazolin-6-yl]-amide;

5-Piperidin-1-yl-pent-2-enoic acid [4(3-bromo-phenylamino)-7-methoxy-quinazolin-6-yl]-amide;
5-Piperidin-1-yl-pent-2-enoic acid [4(3-chloro-4-fluoro-phenylamino)-7-ethoxy-quinazolin-6-yl]-amide;
5-Piperidin-1-yl-pent-2-enoic acid [4(3-chloro-4-fluoro-phenylamino)-7-propoxy-quinazolin-6-yl]-amide;
5-(4-Fluoro-piperidin-1-yl)-pent-2-enoic acid [4-(3-chloro-4-fluoro-phenylamino)-7-methoxy-quinazolin-6-yl]-amide;
5-(3-Fluoro-piperidin-1-yl)-pent-2-enoic acid [4-(3-chloro-4-fluoro-phenylamino)-7-methoxy-quinazolin-6-yl]-amide;
5-(2-Fluoro-piperidin-1-yl)-pent-2-enoic acid [4-(3-chloro-4-fluoro-phenylamino)-7-methoxy-quinazolin-6-yl]-amide;
5-Morpholin-4-yl-pent-2-enoic acid [4(3-chloro-4-fluoro-phenylamino)-7-methoxy-quinazolin-6-yl]-amide;
5-Azepan-1-yl-pent-2-enoic acid [4-(3-chloro-4-fluoro-phenylamino)-7-methoxy-quinazolin-6-yl]-amide;
5-Piperidin-1-yl-pent-2-enoic acid [4-(3-chloro-4-fluoro-phenylamino)-7-trifluoromethoxy-quinazolin-6-yl]-amide;
5-Piperidin-1-yl-pent-2-enoic acid [4-(3-chloro-4-fluoro-phenylamino)-7-fluoromethoxy-quinazolin-6-yl]-amide;
5-Piperidin-1-yl-pent-2-enoic acid [4-(3-chloro-4-fluoro-phenylamino)-7-fluoroethoxy-quinazolin-6-yl]-amide;
5-Piperidin-1-yl-pent-2-enoic acid [4-(3-chloro-4-fluoro-phenylamino)-7-(2-fluoro-ethylsulfanyl)-quinazolin-6-yl]-amide;
5-Piperidin-1-yl-pent-2-enoic acid [4-(3-chloro-4-fluoro-phenylamino)-7-trifluoroethoxy-quinazolin-6-yl]-amide;
5-Piperidin-1-yl-pent-2-enoic acid [4-(3-chloro-4-fluoro-phenylamino)-7-difluoroethoxy-quinazolin-6-yl]-amide;
5-Piperidin-1-yl-pent-2-enoic acid [4-(3-chloro-4-fluoro-phenylamino)-7-(3-morpholin-4-yl-propoxy)-quinazolin-6-yl]-amide;
5-Piperidin-1-yl-pent-2-enoic acid [4(3-chloro-4-fluoro-phenylamino)-7-(2-piperidin-1-yl-ethoxy)-quinazolin-6-yl]-amide;
6-Piperidin-1-yl-hex-2-enoic acid [4-(3-chloro-4-fluoro-phenylamino)-7-methoxy-quinazolin-6-yl]-amide;
6-Piperidin-1-yl-hex-2-enoic acid [4-(3-chloro-4-fluoro-phenylamino)-7-methylsulfanyl-quinazolin-6-yl]-amide;
6-Piperidin-1-yl-hex-2-enoic acid [4-(3-chloro-4-fluoro-phenylamino)-7-methylamino-quinazolin-6-yl]-amide;
6-Piperidin-1-yl-hex-2-enoic acid [4-(3-chloro-4-fluoro-phenylamino)-7-ethoxy-quinazolin-6-yl]-amide;
6-Piperidin-1-yl-hex-2-enoic acid [4-(3-chloro-4-fluoro-phenylamino)-7-fluoroethoxy-quinazolin-6-yl]-amide; and a pharmaceutically acceptable salt of any of the aforementioned compounds.

8. A compound which is

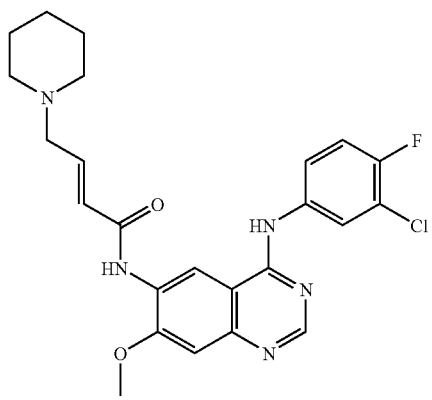

or a pharmaceutically acceptable salt thereof.

9. A pharmaceutical composition comprising a compound which is

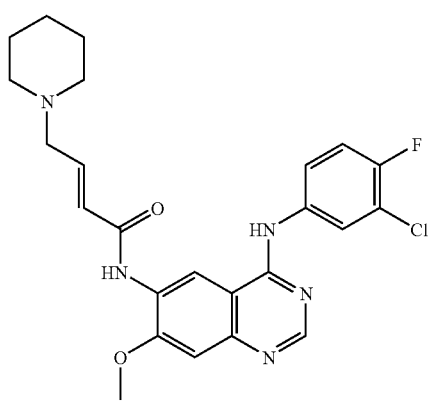

or a pharmaceutically acceptable salt thereof, and a pharmaceutically acceptable carrier.

* * * * *

Disclaimer

7,772,243 B2 - Stephen Alan Fakhoury, Saline; Helen Tsenwhei Lee, Ann Arbor; Jessica Elizabeth Reed Ann Arbor; Kevin Matthew Schlosser, Ann Arbor; Karen Elaine Sexton, Chelsea; Haile Tecle, Ann Arbor; Roy Thomas Winters, Pinckney, all of MI (US). 4-PHENYLAMINO-QUINAZOLIN-6-YL-AMIDES. Patent dated August 10, 2010. Disclaimer filed March 13, 2025, by the assignee, Warner-Lambert Company LLC.

I hereby disclaim the terminal part of this patent beginning on the date May 6, 2028.

*(Official Gazette, May 6, 2025)*